(12) United States Patent
Macy, Jr. et al.

(10) Patent No.: US 9,775,980 B2
(45) Date of Patent: Oct. 3, 2017

(54) VALVED ENTERAL ADMINISTRATION ASSEMBLY

(71) Applicant: Hospi Corporation, Newark, CA (US)

(72) Inventors: Bradford Macy, Jr., Concord, CA (US); Igal Ladabaum, San Carlos, CA (US); John Eaton, Palo Alto, CA (US)

(73) Assignee: Hospi Corporation, Newark, CA (US)

( * ) Notice: Subject to any disclaimer, the term of this patent is extended or adjusted under 35 U.S.C. 154(b) by 11 days.

(21) Appl. No.: 14/372,906

(22) PCT Filed: Feb. 1, 2013

(86) PCT No.: PCT/US2013/024372
§ 371 (c)(1),
(2) Date: Jul. 17, 2014

(87) PCT Pub. No.: WO2013/116670
PCT Pub. Date: Aug. 8, 2013

(65) Prior Publication Data
US 2015/0045746 A1 Feb. 12, 2015

Related U.S. Application Data

(60) Provisional application No. 61/632,876, filed on Feb. 1, 2012.

(51) Int. Cl.
*A61M 5/00* (2006.01)
*A61M 25/16* (2006.01)
(Continued)

(52) U.S. Cl.
CPC ............ *A61M 39/16* (2013.01); *A61J 7/0053* (2013.01); *A61J 15/0092* (2013.01);
(Continued)

(58) Field of Classification Search
CPC .. A61M 39/10; A61M 39/1011; A61M 39/26; A61M 39/16; A61M 2206/14;
(Continued)

(56) References Cited

U.S. PATENT DOCUMENTS 3,409,015 A 11/1968 Swanson
3,416,567 A 12/1968 von Dardel et al.
(Continued)

FOREIGN PATENT DOCUMENTS

DE 202008009245 U1 10/2008
EP 2075032 A1 7/2009
(Continued)

OTHER PUBLICATIONS

Bard Corp.; Colon/Rectal Tubs (product list); downloaded from http://www.bardmedical.com/products/loadproduct.aspx?prodID=340 on May 10, 2010; 2 pgs.

*Primary Examiner* — Rebecca E Eisenberg
(74) *Attorney, Agent, or Firm* — Shay Glenn LLP

(57) ABSTRACT

An enteral administration assembly for administering fluids through an enteral device. The administration assembly comprising an inlet, an outlet, and a valve mechanism between the inlet and outlet. The inlet is configured to interlock with only an enteral device to form a sealed connection allowing the passage of fluid between the enteral device and the inlet. The assembly may include a valve or turbulating mechanism comprising a valve and at least one turbulator adapted to change the direction of fluid flowing through the assembly to prevent clogging and flocculation of administered substances.

17 Claims, 17 Drawing Sheets

(51) Int. Cl.
  *A61M 25/18* (2006.01)
  *A61M 39/00* (2006.01)
  *A61M 39/10* (2006.01)
  *A61M 39/16* (2006.01)
  *A61M 39/26* (2006.01)
  *A61M 31/00* (2006.01)
  *A61J 7/00* (2006.01)
  *A61J 15/00* (2006.01)

(52) U.S. Cl.
  CPC ........ *A61M 31/00* (2013.01); *A61M 39/1011* (2013.01); *A61M 39/26* (2013.01); *A61M 2206/14* (2013.01); *A61M 2210/1067* (2013.01)

(58) Field of Classification Search
  CPC ............ A61M 239/1094; A61M 31/00; A61M 39/02; A61M 2039/0202; A61M 2039/0205; A61J 15/0092; A61J 7/0053
  See application file for complete search history.

(56) References Cited

U.S. PATENT DOCUMENTS

| | | | |
|---|---|---|---|
| 3,509,884 A | 5/1970 | Bell | |
| 4,119,098 A | 10/1978 | Bolduc et al. | |
| 4,403,982 A | 9/1983 | Clayton | |
| 4,516,578 A | 5/1985 | Shuffield | |
| 4,535,820 A | 8/1985 | Raines | |
| 4,946,448 A | 8/1990 | Richmond | |
| 4,966,199 A | 10/1990 | Ruschke | |
| 5,098,405 A | 3/1992 | Peterson et al. | |
| 5,197,950 A | 3/1993 | Clayton | |
| 5,312,343 A | 5/1994 | Krog et al. | |
| 5,509,929 A | 4/1996 | Hascoet et al. | |
| 5,843,723 A | 12/1998 | Dubensky, Jr. et al. | |
| 5,846,216 A | 12/1998 | Gonzales et al. | |
| 5,910,128 A | 6/1999 | Quinn | |
| 6,077,243 A | 6/2000 | Quinn | |
| 6,102,929 A | 8/2000 | Conway et al. | |
| 6,165,168 A | 12/2000 | Russo | |
| 6,468,245 B2 | 10/2002 | Alexandersen | |
| 6,569,132 B1 | 5/2003 | Dvärsäter | |
| 6,623,453 B1 | 9/2003 | Guibert et al. | |
| 6,652,441 B2 | 11/2003 | Weinberger et al. | |
| 7,022,105 B1 | 4/2006 | Edwards | |
| 7,387,638 B2 | 6/2008 | Gonzales | |
| 8,323,255 B2 | 12/2012 | Martino et al. | |
| 8,529,543 B2 | 9/2013 | Macy, Jr. | |
| 8,603,029 B2 | 12/2013 | Macy, Jr. | |
| 2003/0060799 A1 | 3/2003 | Arenberg et al. | |
| 2003/0153897 A1* | 8/2003 | Russo | A61M 39/045 604/537 |
| 2004/0039348 A1 | 2/2004 | Kim et al. | |
| 2004/0124389 A1 | 7/2004 | Phillips | |
| 2004/0236365 A1 | 11/2004 | Cioanta et al. | |
| 2005/0054996 A1 | 3/2005 | Gregory | |
| 2005/0267415 A1 | 12/2005 | Jacques | |
| 2006/0178645 A1 | 8/2006 | Peppel | |
| 2006/0276746 A1 | 12/2006 | Burnside et al. | |
| 2007/0073216 A1 | 3/2007 | McAuliffe et al. | |
| 2009/0099546 A1* | 4/2009 | Macy, Jr. | A61M 25/0068 604/514 |
| 2009/0205658 A1* | 8/2009 | Tanaka | A61M 1/04 128/203.15 |
| 2009/0232586 A1 | 9/2009 | Diodati et al. | |
| 2009/0259175 A1* | 10/2009 | Nordgren | A61M 39/24 604/30 |
| 2010/0121309 A1 | 5/2010 | Macy, Jr. | |
| 2014/0066848 A1 | 3/2014 | Macy | |

FOREIGN PATENT DOCUMENTS

| | | |
|---|---|---|
| EP | 2140907 A1 | 1/2010 |
| EP | 2168611 A1 | 3/2010 |
| WO | WO 03/018105 A1 | 3/2003 |
| WO | WO2007/120620 A2 | 10/2007 |

* cited by examiner

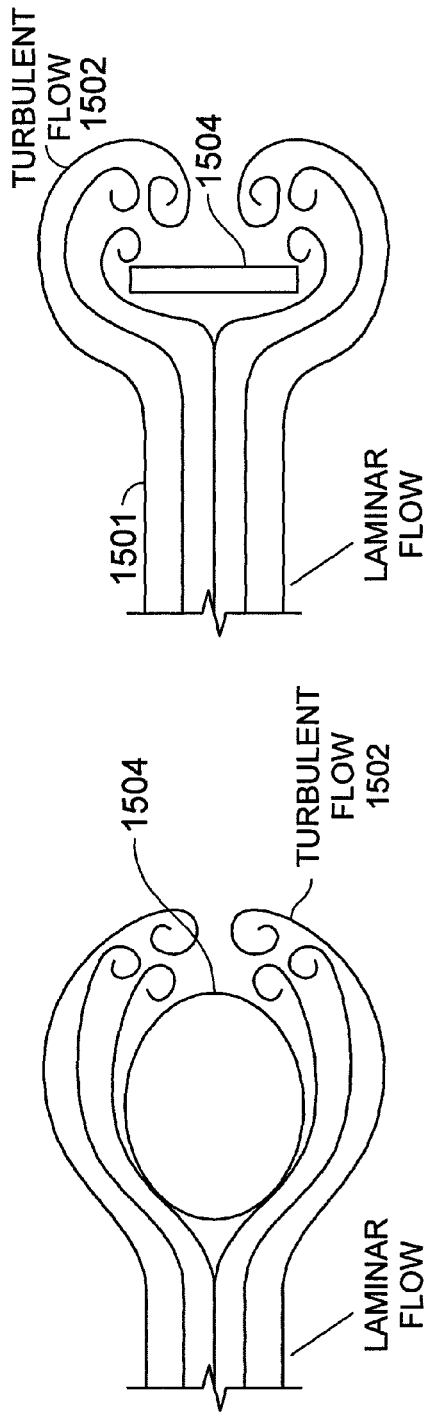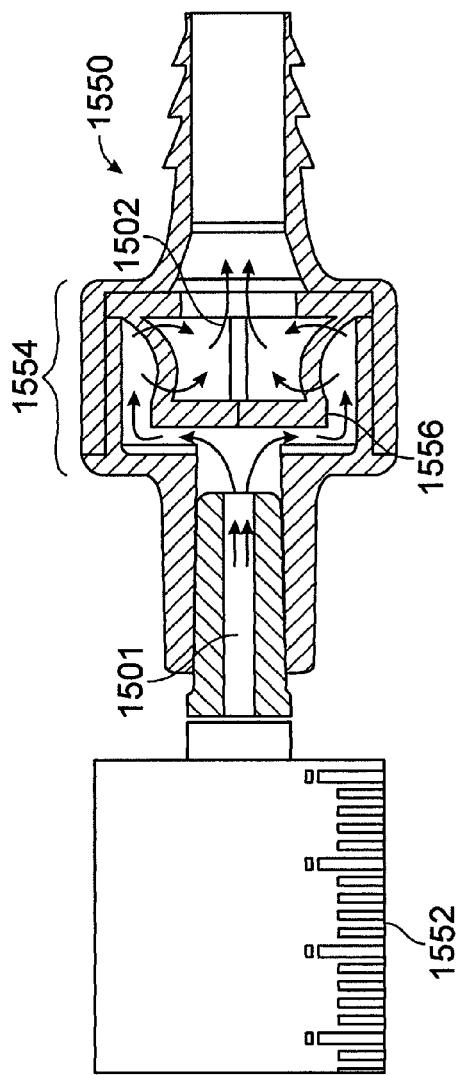
FIG. 5A
FIG. 5B
FIG. 5C

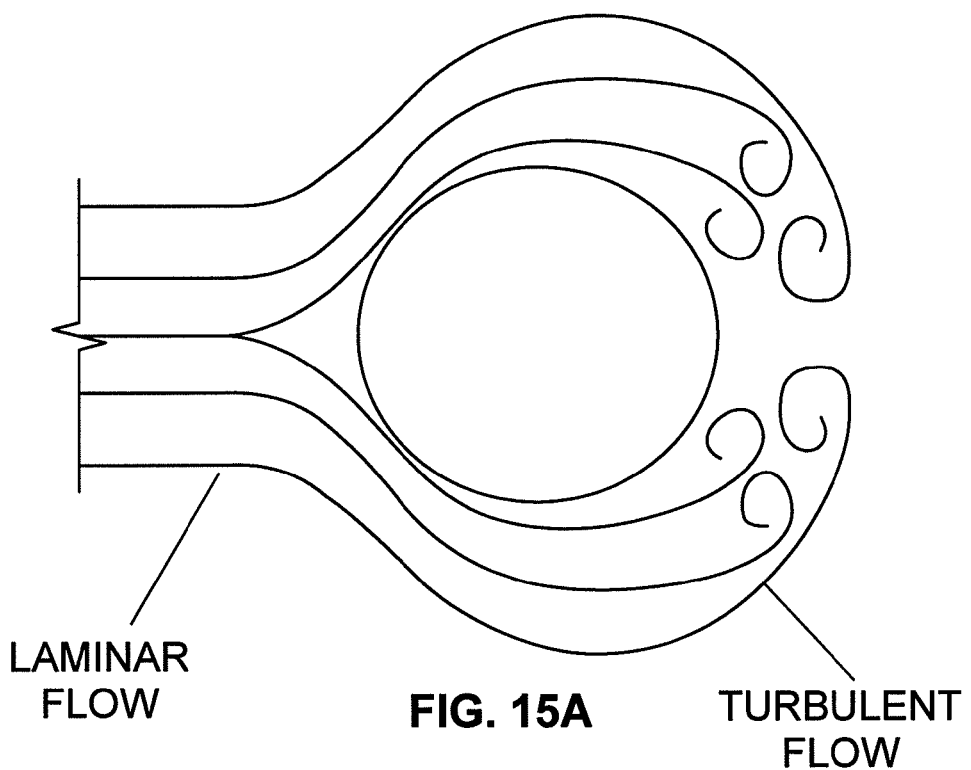
LAMINAR FLOW  FIG. 15A  TURBULENT FLOW
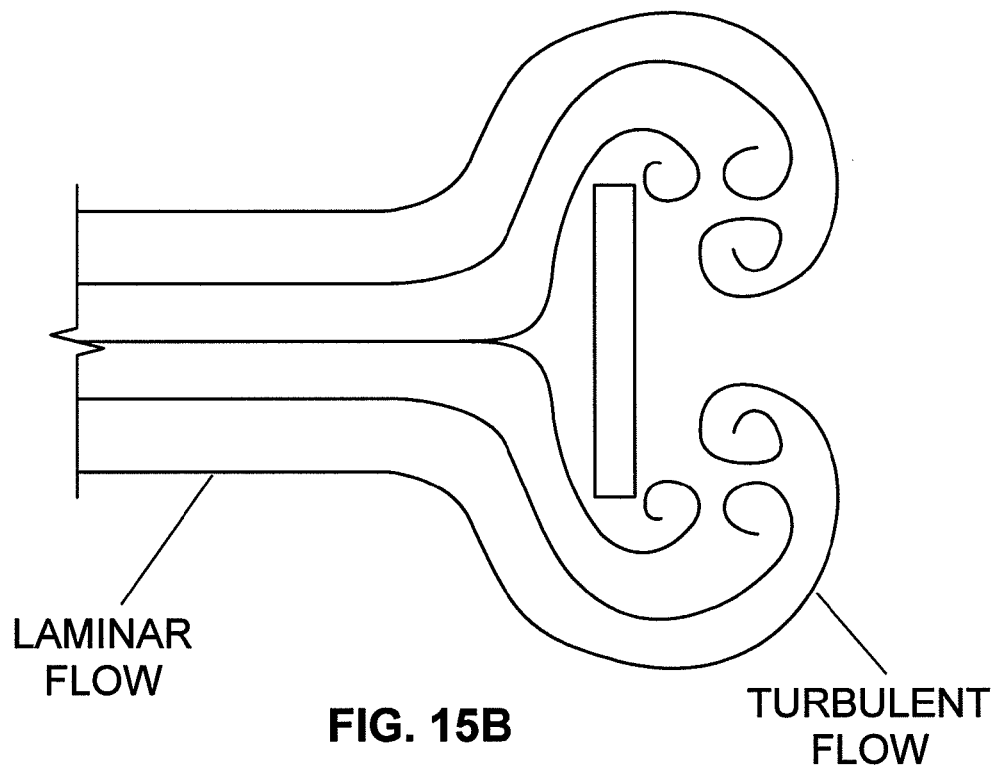
LAMINAR FLOW  FIG. 15B  TURBULENT FLOW

VALVED ENTERAL ADMINISTRATION ASSEMBLY

CROSS REFERENCE TO RELATED APPLICATIONS

This application claims priority to U.S. Provisional Patent Application No. 61/632,876, filed on Feb. 1, 2012, titled "TURBULENT FLOW VALVE AN APPARATUS AND METHOD FOR CREATING TURBULENT FLUID FLOW WITHIN AN ENCLOSED SPACE," which is herein incorporated by reference in its entirety. This application may be related to U.S. application Ser. No. 12/235,601, filed on Sep. 23, 2008, titled APPARATUSES AND METHODS FOR MEDICATION ADMINISTRATION, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This invention relates generally to methods, systems, and apparatuses for the enteral delivery of medications to patients. More particularly, embodiments contemplated provide for valved enteral administration assemblies or ports having improved patient safety features to prevent misconnection of medical devices and misadministration of medication to patients.

BACKGROUND

Various tubular devices exist to access different portions of the gastrointestinal tract. For example, oro-gastric or naso-gastric tubes exist to suction secretions and fluid from the stomach as well as to deliver fluids and feeding solutions. Bowel waste management systems exist to collect the feces of incontinent patients. Devices whose lumens communicate with the gastrointestinal tract, broadly referred to as enteral devices, are also used to deliver medication. For example, U.S. Pat. Nos. 8,123,732 and 7,147,627 describe a port for a bowel management system that can be used to administer medication. Indeed, the administration of medication into the rectum is playing an increased role in medicine, especially in palliative care for symptom control.

Despite the increased interest in enteral administration for medical care, there have recently been serious adverse outcomes related to the misconnection of various medical devices to incorrect ports of medical tubes. Significant complications including deaths have occurred when feeding solutions, non-sterile or suspended medications meant to be given into the enteral tract have been inadvertently injected into the blood stream. Indeed, ISO standards currently demand, and the FDA will soon require, that ports for enteral devices be rigid, non-flexible, and unable to connect to Luer type connections and even other devices such as medical oxygen, and suction apparatuses in order to avoid misconnection and injury to patients.

It is of utmost importance to provide a medication port for enteral devices which does not mate to a Luer type syringes or other medical devices. A rigid female port which connects only to an enteral delivery device, such as an enteral adaptor or enteral tapered syringe, and is incapable of connection to a Luer type syringe is one way to minimize the probability of introducing enteral solutions intravenously. As such, there is a need for an improved medication administration port or assembly to prevent potential health and safety issues associated with these types of enteral devices. Therefore, in one aspect, embodiments described herein provide for an administration port/assembly that connects only with enteral specific devices (e.g. enteral syringes) for medication administration to the gastrointestinal tract.

Another challenge for enteral patient care has been the spread of infection in healthcare environments and the community at large. Antibiotic resistant infections are a $20 billion dollar problem in the United States. It is of utmost importance that devices engineer safety features within the design which minimize the risk of bio-hazardous contamination of the environment. Medication ports or assemblies attached to body cavities that do not need to extract fluid from the body cavity should be designed in such a way that retrograde flow cannot occur. Delivery assemblies such as ports on devices which only administer medication should be one way, for delivery only. Especially when these tubes enter orifices which contain high levels of microbes such as the rectum, they should not allow for any retrograde flow to decrease the possibility of environmental contamination of bio-hazardous substances.

Although preventing retrograde flow in parenteral medication and fluid administration has been addressed to some degree, the same attention has not been given to enteral administration. For example, U.S. Pat. No. 3,416,567 and U.S. Pat. No. 5,098,405 teach valves for parenteral infusions, but do not teach valves for enteral application. Furthermore, the valves taught for parenteral administration would fail in the context of enteral administration because of the differences between the sterile, controlled solutions used in parenteral administration and enteral formulations.

Typically the port of enteral medical devices through which medication can be administered has been a non-valved, simple bi-directional port, sometimes including a capping mechanism which is used for multiple purposes including irrigation, fluid and medication administration, suctioning, and sampling. Furthermore, these ports are often soft and flexible, and mate non-restrictively with enteral, catheter tip, and luer type syringes and connectors. The need for a one-way valved main or side port which can only connect to an enteral device with enteral tip dimensions has not been addressed for enteral devices. As such, in another aspect, some described embodiments herein provide for an enteral-only medication administration port or assembly with a one or uni-directional valve for use with an enteral device. Advantageously, a one-directional valve has the added benefit of ensuring that the appropriate dose of the medication is administered without any leakage out of the enteral device (e.g. rectal tube).

In addition to the above, there is also a need for an enteral delivery device such as a port and/or delivery assembly that maintains the suspended form of viscous fluids for enteral administration to a patient. Unlike medications given intravenously which are administered in solution or in suspensions of very small particulate size (usually less than 1 micron) form, medications given enterally are often large particulate suspensions with particulate sizes 100 of microns in diameter. For instance, solid medications are many times crushed and suspended in water to be injected through these devices which can have a very large particulate size. These substances can clog valves, or cause them to stick in the open position unless the interior of the valve is designed allow these medications to remain suspended as they pass through the valve.

Many valves exist which facilitate parenteral injection of fluids into the body as opposed to enteral administration. These parenteral valves usually open when a syringe or intravenous connector is attached and close when they are removed. They are usually attached to a fluid transmission tube of some type, such as intravenous lines for injection into the blood stream. Existing parenteral valves are limited in their utility as they are not designed to produce turbulent flow. Turbulent flow is important within a valve used in a device that transmits enteral medication formulations. Turbulent flow keeps the walls of the valve from building up particles which can eventually clog the valve and serve as a breeding ground for bacteria.

Turbulent flow is especially important for enteral devices which administer fluids in suspension, via the gastrointestinal tract (e.g. oral, gastric, and rectal delivery). If flow is not turbulent through an enteral device the particles in suspension settle or flocculate, causing clogs. Emulsions also cause clogging. Although they do not settle and are more stable than suspensions, they can cause residue buildup on the wall of the valve which eventually clogs the device. Residue buildup can cause bacterial growth and is a cause of bacteremia by intravenous devices. Total parenteral nutrition (TPN) is an example of an emulsion given intravenously. Its high nutrient composition makes it a strong catalyst for bacterial growth. Blood is also an emulsion and is the most common reason for clogging in intravenous lines, and also encourages bacterial growth.

As mentioned, an enteral fluid delivery device, such as an enteral administration assembly or port, is needed which will not clog or allow for residue buildup within itself or within the fluid transmission tube immediately adjacent to it. Creating such a device must take into account the complex fluid dynamics associated with emulsions and suspensions. The first important consideration is the type of flow within the device and through the fluid transmission tube. Turbulent flow favors a stable suspension as opposed to laminar flow. Destabilization of the suspension or emulsion can occur more easily in laminar flow as viscous forces are encouraged over inertial forces, causing flocculation, coalescence, or sedimentation as particles begin to congregate.

Another benefit of turbulent flow has to do with the interaction of the fluid with the wall of the delivery device itself. In laminar flow, suspensions and emulsions can settle easier, as flow near the wall of the delivery device slows to basically a complete stop. This decreased flow velocity zone is called the boundary layer. With turbulent flow, random movement of fluid in different vectors and an increased overall kinetic energy creates a cleaning or scouring action against the wall of the device, as particles and water hit the wall from different trajectories loosening and removing deposits. In laminar flow on the other hand, fluid moves parallel to the wall slowing to a complete stop at the boundary layer. This encourages destabilization and formation of deposits on the device walls which can eventually form a clog, and also encourages bacterial growth and biofilm formation. In intravenous devices, blood cells tend to accumulate on the walls of valves and the inner lumen of the line creating a high potential for bacterial growth and can cause sepsis in the patient.

Another consideration in the delivery device design is the diameter of the passageway. The potential to create turbulent flow increases with passageway diameter and fluid velocity. This is shown in the Reynolds equation which gives us a measure of the ratio of inertial forces to viscous forces. Thus, the Reynold's number can predict laminar vs. turbulent flow. As discussed above, dynamic states in which viscous forces overpower inertial forces favor laminar flow. Laminar flow occurs at lower Reynolds numbers and turbulent flow occurs with higher numbers as shown in the equation below. Both tube diameter and velocity are directly proportional to the Reynold's number.

Reynolds Equation $$Re = \frac{\rho v D_H}{\mu};$$

where:
$D_H$ is the inner diameter of the tube or device.
v is the mean velocity of the object relative to the fluid
$\mu$ is the dynamic viscosity of the fluid
$\rho$ is the density of the fluid
Re is the Reynolds number With the small diameter of most medical tubes, valve assemblies, and intravenous lines, turbulent flow is almost impossible to achieve without a turbulator within the lumen which increases the inertial forces of particles moving through. A turbulator is simply a device which turns laminar flow into turbulent flow. It increases the kinetic force component within the system. But in order to create turbulence even with the assistance of a turbulating device, fluid velocity within the lumen must be fast enough to generate the kinetic energy needed to transition flow from laminar to turbulent. Tube diameter has a powerful effect on flow. If the diameter within, for example, an enteral administration device becomes too small, flow slows, encouraging laminar flow and destabilization, or stops completely as there will eventually not be enough pressure to force the fluid mixture through the device for delivery to the patient tube. In other words, turbulent flow can easily transition to laminar flow if the diameter of a tube through which a fluid travels decreases, and if the kinetic energy of the suspended mixture is allowed to dissipate.

Given these considerations, another aspect of the invention provides for enteral delivery devices or assemblies (e.g. ports) that include turbulators for creating turbulent fluid flow to maintain suspended mixtures and prevent sedimentation or flocculation.

In summary, embodiments described provide for, among other things, an improved valved enteral administration assembly such as a port for delivery of medications to the rectum or other parts of the gastro-intestinal tract, which are capable of transmitting emulsions, large particulate suspensions, and viscous solutions typical of enteral medications, and which can be permanently disposed on the enteral medical device. In some variations, the enteral administration port or assembly is incompatible with Luer connectors. Additionally, some embodiments include a valve or valve mechanism which provides for uni-directional flow and prevents retrograde flow—delivering substances to the body cavity, but not allowing for withdrawal from the body cavity. For those cases where bi-directional flow is desired such as a sampling-irrigation port, as opposed to simply a medication port, an embodiment with a bi-directional valve is also contemplated and described herein.

SUMMARY OF THE DISCLOSURE

Systems, methods, and apparatuses for improved enteral administration are disclosed. The disclosed invention, which may be referred to (non-exhaustively) as a port, enteral delivery assembly, enteral administration system, or variations thereof, allows for a sealed connection between an enteral-type device (e.g. enteral tapered syringe or enteral connector/adaptor) and the port to prevent misadministration of medication or other substances to the patient.

In particular, in one aspect, embodiments described provide for an optimized valved enteral administration port which combines several features essential to the safe and effective delivery of numerous potential forms of enterally delivered medications. In some variations, the medication port could be permanently disposed, for example, on the main lumen of a device which delivers medication to the rectum to improve the safety and effectiveness of medication delivery to the rectum. In other variations, the enteral medication delivery port could also improve any enteral tube, for example feeding tubes or fecal continence tubes, when used as a side port to safely deliver medications by not allowing Luer locking syringes to connect to the device, only allowing enteral syringes to connect, and preventing retrograde flow out of the medication port.

In further embodiments, the enteral port optimizes safe and effective administration of medication to the gastrointestinal tract. This can be accomplished in several ways. For example, in any of the preceding embodiments, the port mates only with an enteral tapered syringe or enteral connector and is not adaptable to a Luer tapered syringe or connectors. In further embodiments, the port is designed to be permanently placed on the enteral device in a readily manufacturable manner.

Additionally, in any of the preceding embodiments, medication cannot be delivered into the port with a Luer tapered syringe. In further embodiments, the port is able to produce and maintain turbulent flow to decrease settling of suspended particles and decrease the buildup of residue and biofilm formation on the walls of the valve. In additional embodiments, the port and its valve do not clog when substances such as both small and large particulate suspensions, and thicker more viscous substances such as oils, emulsions are injected through the device. In any of the preceding embodiments, the port valve is configured to avoid getting lodged open with suspended medications or particles which would allow for possible leakage of fluids.

Furthermore, in any of the preceding embodiments, the port valve can be configured for one way delivery only, to avoid medication dose or bio-hazardous material from being inadvertently extracted from the device. However, alternative embodiments provide for bi-directional flow.

In another aspect, the embodiments described provide for an enteral fluid delivery device having a turbulent flow valve assembly or mechanism that generates turbulent flow and facilitates transmission of fluids in suspension or emulsion, which decreases the potential for clogging and residue buildup.

In some embodiments, the turbulent flow valve mechanism opens when a syringe or intravenous tubing is attached to allow a fluid within said syringe or intravenous tubing to be injected into and through the valve, and closes when said syringe or intravenous tubing is removed to keep the injected fluid and body fluids from leaking out. This device can also be used effectively to facilitate transmission of any suitable fluid other than suspensions or emulsions into the body, and to remove fluids from the body.

The non-clogging, residue resistant utility is achieved through several design features. For example, in some embodiments, several specially designed turbulators within the enteral administration assembly or device create turbulent flow. In some embodiments, the turbulent flow inhibits suspensions from destabilizing and/or residue from building on the walls of the assembly. In further embodiments, the diameter of the internal portion of the assembly through which the fluid flows is designed to be as large, or larger than the diameter of the syringe tip through which the fluid enters the enteral administration assembly, facilitating the turbulent flow of fluid through the assembly and into the fluid transmission tube. Additionally, in any of the preceding embodiments, a turbulator at the distal end of the assembly produces turbulent flow which is transmitted into the fluid transmission tube, decreasing the potential for clogging and residue buildup within said tube.

In another aspect, the embodiments described provide for a valved enteral administration assembly including a rigid inlet configured to mate only with a first enteral device; a rigid outlet configured to mechanically connect to a lumen of a second enteral device; and a valve mechanism between the inlet and outlet.

In any of the preceding embodiments, the rigid inlet has an inlet opening and the rigid outlet comprises an outlet opening. In further embodiments, the outlet is configured to permanently interlock to said lumen of the second enteral device. In any of the preceding embodiments, the rigid inlet includes holes therein configured to seal when the rigid inlet is mated with the first enteral device.

In any of the preceding embodiments, the inlet is configured to prevent a sealed connection with a luer mechanism. In other embodiments, the inlet has a tubular lumen and an inner surface having at least one hole between the valve mechanism and an opening of the inlet.

Additionally, in any of the preceding embodiments, the outlet can include an outside surface having a plurality of surface features adapted to maintain the mechanical connection with the lumen of the second enteral device. In further embodiments, the outlet has a tapered outer surface having a plurality of protrusions adapted to interlock the lumen of the second enteral device.

In some embodiments, an inner surface of the inlet defines a lumen having a tapering cross-section. In any of the preceding embodiments, the inlet lumen has a first diameter proximal to an inlet opening that is greater than a second diameter proximal to the valve mechanism. In some embodiments, the diameter of the inlet lumen decreases from an opening of the inlet to the valve mechanism along a longitudinal axis of the port, the diameter decreasing by an angle of about 1.4 degrees to about 1.7 degrees.

In any of the preceding embodiments, the valve mechanism is configured to prevent retrograde flow through the inlet. In any of the preceding embodiments, the valve mechanism is configured for one-directional delivery. In some embodiments, valve mechanism is configured for bi-directional fluid flow. In additional embodiments, the valve mechanism is configured to produce and maintain turbulent flow of fluids flowing therethrough.

In any of the preceding embodiments, the valve mechanism includes a valve membrane positioned against an opening of the inlet; a base abutting an opening of the outlet; and a plurality of interposing resilient members connecting the valve membrane and base. In any of the preceding embodiments, the valve mechanism can include a turbulator adapted to produce turbulent fluid flow through the assembly. In some embodiments, the valve mechanism base is a turbulator. In any of the preceding embodiments, the plurality of interposing resilient members are turbulators. In some embodiments, the plurality of interposing resilient members are configured to deflect when positive pressure is applied to the membrane to thereby allow fluid flow therethrough.

In any of the preceding embodiments, the valve mechanism includes an opening element attached to the membrane, the opening element configured to open the valve membrane when depressed by an enteral device (e.g. first enteral device). In some embodiments, the opening element has a set of prongs.

In any of the preceding embodiments, the inlet is configured to mate only with an enteral tapered syringe.

In another aspect, embodiments described provide for an enteral administration system including an administration assembly having an inlet portion and an outlet portion, the inlet portion configured to interlock with an enteral tapered syringe to form a sealed connection allowing the passage of fluid between the enteral syringe and the inlet portion; and a valve assembly. In some embodiments, the valve assembly includes a valve member and a turbulator adapted to change the direction of fluid flowing through the valve member.

In any of the preceding embodiments, the inlet portion comprises a rigid material. In some embodiments, the inlet portion includes a first opening and a second opening, and a tapering inner tube between said openings, the inner tube tapering by about 1.4 degrees to about 1.7 degrees along a length of the inlet portion. In any of the preceding embodiments, the inlet portion is formed of a tube having a proximally-extending inner tapered configuration, the tube adapted to mate only with an enteral tapered syringe.

In any of the preceding embodiments, the outlet portion is adhered to a lumen of an enteral device. In some embodiments, the outlet portion comprises mechanical features on an outer surface of the outlet portion for gripping a lumen of an enteral device.

In any of the preceding embodiments, the valve assembly includes a spring element coupled to the valve member, the spring element configured to depress to thereby open said valve member. In some embodiments, the spring element is positioned between the inlet and outlet portions.

In any of the preceding embodiments, a plurality of resilient turbulators are coupled to the valve member, wherein when deflected the turbulators open the valve member to provide a turbulent fluid flow-through path.

In any of the preceding embodiments, a slit is located along the inlet portion length, wherein a sealed connection is formed distal of the slit.

In any of the preceding embodiments, the smallest width of a fluid channel in the valve assembly is greater than the diameter of a tip opening on the enteral syringe.

In another aspect, embodiments provide for a valve system for enteral fluid administration having a housing body; and a turbulating mechanism within the housing body. In any of the preceding embodiments, the turbulating mechanism includes a valve member, a first turbulating element attached to a first side of the valve member, and a second turbulating element attached to a second side of the valve member.

In any of the preceding embodiments, the housing body has an end configured to interface with a syringe. In some embodiments, the housing body includes a hollow tube having a first diameter in a first section and a second diameter in a second section, the second diameter being greater than the first diameter. In further embodiments, the second section is configured to interface with a lumen of an enteral device.

In any of the preceding embodiments, the first turbulating member is positioned within an inlet orifice of the housing body. In further embodiments, the first turbulating member includes a set of prongs.

In any of the preceding embodiments, the second turbulating member has a resilient member positioned between the valve member and an outlet opening of the housing body. In some embodiments, the second turbulating member includes a plurality of compressible resilient members.

In any of the preceding embodiments, the turbulator is a spring. In some embodiments, one of the turbulators is a spring.

In any of the preceding embodiments, the enteral administration system includes an anchor member having a circular frame and a plurality of struts connecting to the frame. In some embodiments, the anchor member is a turbulator. In further embodiments, the anchor member is configured to hold a fluid transmission tube to the valve system. In other embodiments, the valve system is configured to convert laminar fluid flow into turbulent fluid flow.

In another aspect, embodiments provide for a method of medication administration through an enteral device including the steps of: providing an administration assembly having a hollow inlet section, an outlet section attached to a lumen of the enteral device, and a valve mechanism between the inlet and outlet sections; coupling an enteral tapered syringe to the assembly by forming a mated sealed connection between a tip of the enteral tapered syringe and the inlet section; applying a positive pressure from the enteral tapered syringe to distally depress a valve member of the valve mechanism to form a fluid flow-through path between the assembly and the syringe; and causing turbulent fluid flow as fluid passes through the valve mechanism.

In some embodiments, the method of medication administration includes detaching the administration assembly from the syringe. In further embodiments, the method of medication administration includes applying a negative pressure from the enteral tapered syringe to remove a volume of fluid from the enteral device. In other embodiments, the method of medication administration includes opening the valve member by physically engaging the tip of the enteral tapered syringe with a valve opening element attached to the valve member. In some embodiments, the method may include instilling medication into a patient's body cavity by administering the medication from the enteral tapered syringe through the administration assembly and into the patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5a-5b is a schematic drawing of laminar flow turning turbulent when it hits a turbulator creating an eddy.

FIG. 5c shows a turbulent flow created by a spring body in the valve mechanism of FIG. 4.

FIGS. 15a-15b schematically illustrate laminar flow transitioning to turbulent flow.

DETAILED DESCRIPTION

The following description and drawings are illustrative and are not to be construed as limiting. Numerous specific details are described to provide a thorough understanding. However, in certain instances, well known or conventional details may not be described in order to avoid obscuring the description.

The term "about" when used before a numerical designation, e.g., length, width, dimension, or ranges, indicates approximations which may vary by (+) or (−) 1%.

As discussed above, one of the challenges for enteral patient care has been the significant risk of accidently introducing enteral targeted medication or other substances through non-enteral ports into the patient. Because currently available administration ports are designed to be non-restrictively compatible with a variety of fluid delivery devices such as luer-type or enteral-type syringes, these administration ports do not mitigate against the misadministration of medication. To address this need, novel and improved systems, devices, assemblies, and methods for enteral patient care, specifically enteral fluid delivery are presented.

Figures 1A, 1B:
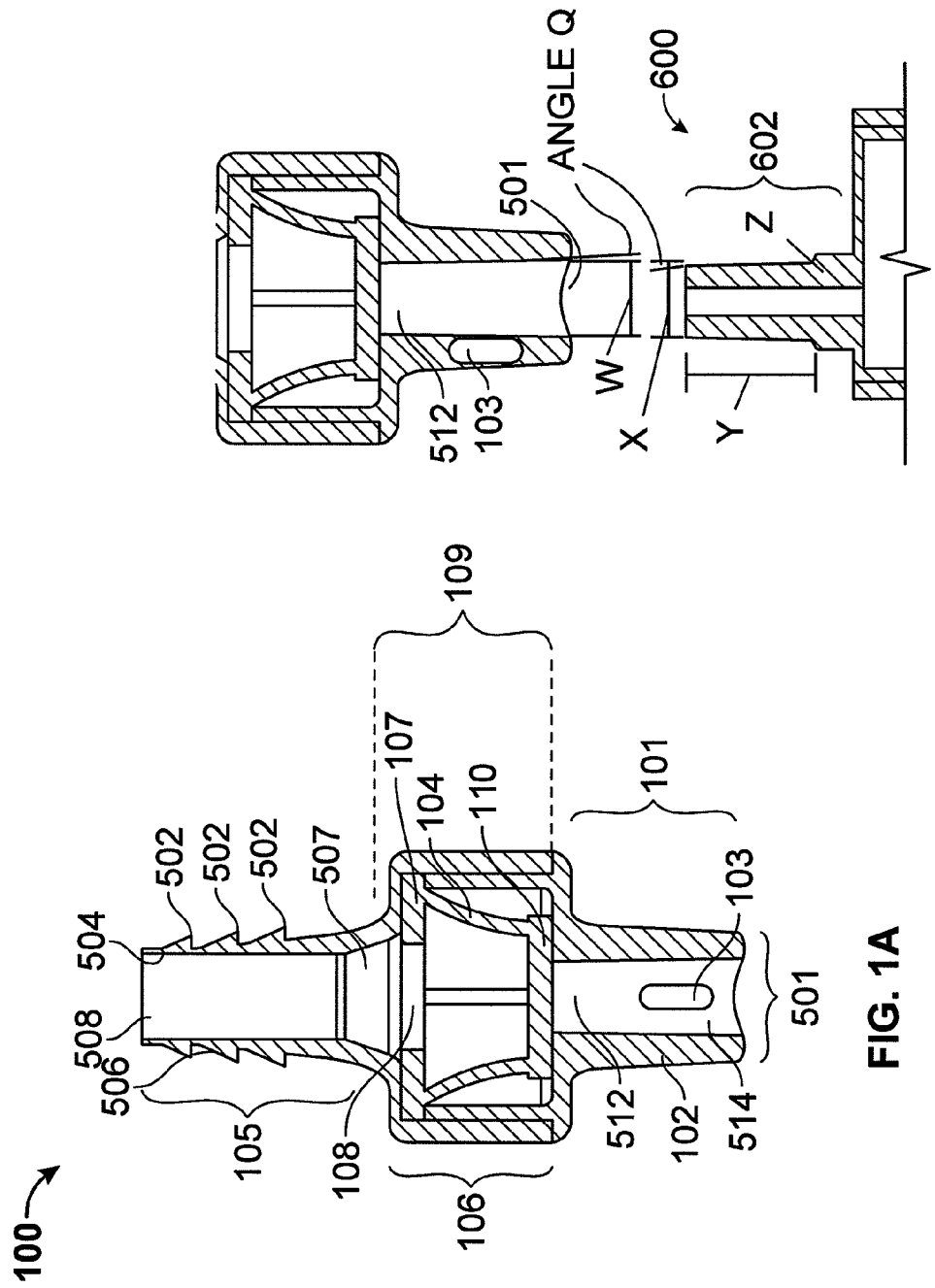
FIG. 1a illustrates a cross-sectional view of one embodiment of an enteral administration assembly and components.
FIG. 1b shows the respective dimensions of one embodiment of the inlet and an enteral tapered syringe.

FIGS. 1a-1b illustrate a general enteral administration assembly or device according to some embodiments. This device may be enteral administration assembly such as a port. As shown, the assembly or port 100 has an inelastic, rigid, or hard plastic inlet (101) and an inelastic, rigid, or hard plastic outlet (105). The outlet 105 is formed from a hollow tube 504 with a first opening 507 and a second opening 508 distal of the first opening 507. The diameter of the tube 504 may be constant or vary along the length of the outlet. FIG. 1a shows a combination of both where a portion of the tube 504 having a relatively constant diameter or width meets with a tapering section near the first opening 507.

Additionally, the outlet 105 has an outer surface 506, which can include mechanical or surface features such as barbs so that it can be easily inserted during production into the medication lumen of the enteral device, but which prevent extraction during use (adhesive may also be used). Other mechanical or surface features include protrusions, recessed portions, non-linear edges, bumps, dips, ridges, grooves, or other suitable features for facilitating the mechanical attachment and connection between the lumen of an enteral device and the assembly/port 100. The outlet 105 may also be designed to have a tapering outer surface 506. As shown in FIG. 1a, the outer surface 506 tapers from first opening 507 toward the second opening 508.

FIG. 1a also illustrates an inlet 101 of the port 100. The inlet 101 includes a first opening 501 and a second opening 512. An inner tubular lumen 514 extends between the first and second openings 501, 512. In some embodiments, the inner lumen 514 tapers distally from the first opening 501 toward the second opening 512 along a length or longitudinal axis of the inlet 100. In other embodiments, the inner lumen 514 of the inlet 101 comprises a first diameter or width at the first opening 501 and a second diameter or width at the second opening 512. The first diameter may be greater than the second diameter.

Advantageously, in some embodiments, the inlet 101 has novel safety design features which ensure that no misconnection or mistaken injection of medication with a luer-type device such as a luer tapered syringe can occur. In some embodiments, the inlet 101 is designed to mate with an enteral-type device only (e.g. enteral connector or enteral tapered syringe). The inlet wall (102) may be made of an inelastic or rigid material such as a hard, inflexible plastic. Once formed and molded, the plastic form of the inlet 101 will not mate with an incompatible shape. For example, the inlet 101 may be formed with a shape that specifically (and/or only) complements the shape of the tapered tip of an enteral syringe. Any other type of delivery device without the appropriate corresponding shape will not fit into the inlet 101 to produce a sealed connection for fluid delivery. This is because the inlet material is sufficiently rigid to avoid deforming or complying to force a mated fit with an incompatible device. In some embodiments, the inlet 101 does not mate with a luer-type device and will not provide adequate sealing. As such, medication cannot be injected under pressure through the port or assembly 100 with any luer type syringe or connector.

FIG. 1b shows the dimensions of the inlet 101 of the port 100 and the dimensions of the tip 602 of an enteral tapered syringe 600 according to some embodiments. The outer diameter of the tip (X) of widely available enteral syringes is about 0.187 in-0.190 in. The length of the tip (Y) of an enteral syringe is about 0.240-0.245 in. The outer diameter of the tip portion at the junction with the syringe body cylinder (Z) is about 0.199-0.204 in. The tapered angle (Q) is about 1.4-1.7 degrees. Given the enteral syringe tip dimensions in this example, the port 100 may have an inlet 101 configured to specifically and restrictively mate with only this type of enteral syringe. In such variations, the inner diameter of the female inlet 101 of the medication administration port (W) may be in the range of about 0.198-0.199 in. In some embodiments, the inlet 101 has a diameter or width about 0.198-0.203 in at the first opening 501. The inner diameter W of the inlet 101 decreases moving distally from the first opening 501 toward the second opening 512. The inner diameter of the female inlet 101 may decrease with a taper angle of ≈Q (or within a range of about 1.4-1.7 degrees).

Figure 2:
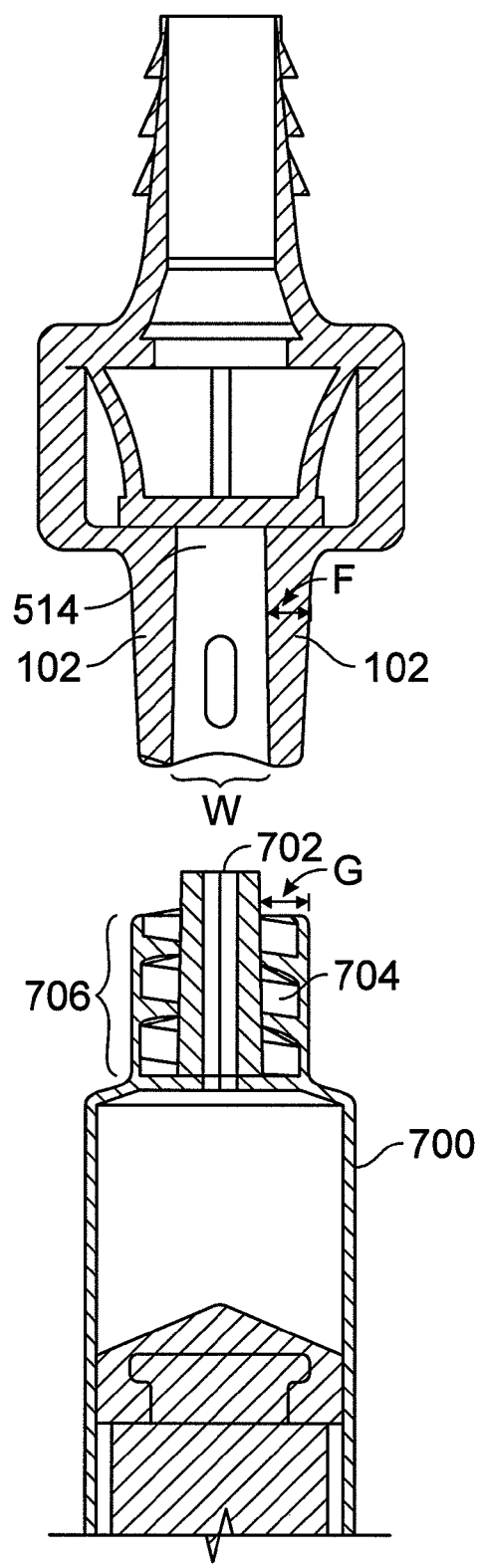
FIG. 2 illustrates the width of the inlet wall of a valve according to some embodiments in comparison to the dimensions of a luer lock syringe.

As discussed, in some embodiments, the inlet 101 is designed to exclude a mated fit with a luer-type device. FIG. 2 illustrates an embodiment where the width F of inlet wall (102) is greater than the space G between a luer tip 702 and the screw notches 704 of a luer locking syringe 700. This, in turn, prevents the luer syringe head 706 from fitting into the inner lumen 514 of the inlet 101. As FIG. 2 illustrates, the distance between the tip and the screw lock of a luer lock connector is less than the thickness of the inlet wall, so the parts do not mate. In other words, the wall thickness of female inlet 101 exceeds the spacing between the male portion and the lock threads of the luer tip. As such, the female inlet wall impedes the advancement of the male luer tip into the female inlet. This safety feature assures that a luer lock syringe cannot be inserted onto the inlet. The majority of luer tapered syringes used in medicine are luer lock type.

Additionally, the inner width or diameter W of the inlet 101 may be designed to be greater than the width of the luer syringe head 706 such that a snug leak-free seal cannot be formed between the luer syringe 700 and the inlet 101. In other embodiments, the inner width or diameter W of the inlet 101 is designed to be smaller than the width of the luer syringe head 706 such that the luer syringe head 706 cannot fit into the inlet lumen 514.

In some embodiments, the enteral administration assembly or port also contains a valve or valve assembly/mechanism for controlling fluid flow through the port. The valve may allow one-directional or bi-directional fluid flow. FIG. 1a shows an example of a valve unit 109 positioned between the inlet 101 and the outlet 105 portions of the port 100. This valve-spring unit (109) is made up of the valve membrane (110), the spring mechanism (104) and the base (107). In the illustrated embodiment, the valve membrane 110 is positioned against or abuts the second opening 512 of the inlet 101. The valve membrane 110 is contiguous with a spring mechanism 104. The entire unit 109 is seated within the valve housing (106). The base of the spring-valve mechanism is seated against the outlet (105) portion of the port, and forms an exit orifice (108) through which fluid transferring through the valve housing enters the port outlet.

In some embodiments, the valve mechanism has a one-way check valve membrane (110) which only allows for fluid flow in one direction so fluid cannot be aspirated out of the enteral administration assembly 100. The valve unit 109 only opens when the pressure is greater on the administration side (inlet) of the valve unit 109, and remains shut when the pressure is equal or greater on the patient side (outlet) of the valve unit 109. For example, the valve membrane 110 can open when an enteral syringe is inserted into the inlet 101 forming an air and fluid tight seal and positive pressure from the syringe is applied. Positive pressure is exerted on the valve membrane 110 from the inlet side bends or deflects the spring mechanism or elements 104 moving the valve membrane 110 distally, and the valve mechanism opens. The valve mechanism 109 shuts when no positive pressure is applied to the valve membrane 110 and fluid flow stops.

The valve membrane 110 and the base 107 may have the same or different dimensions. As shown in FIG. 1a, the valve membrane 110 has a smaller diameter than the base 107. Within the housing 106, unlike the base 107, the valve membrane 110 does not extend across the width of the housing 106. In other embodiments, the valve membrane 110 and the base 107 may have the same dimensions.

Figure 4:
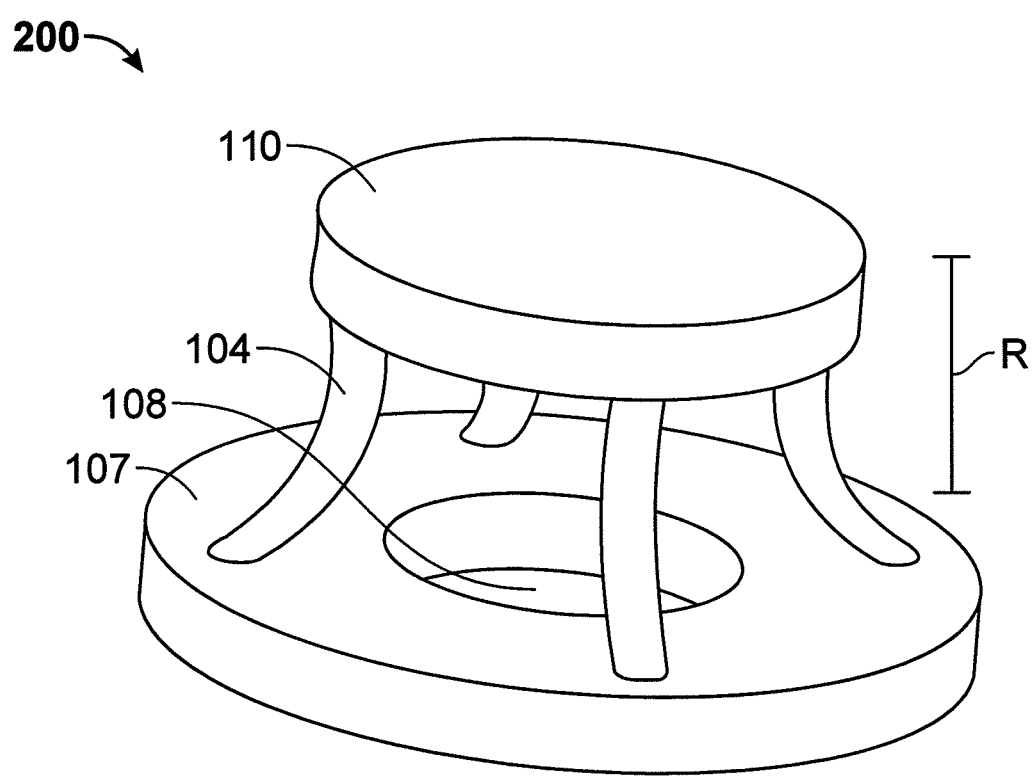
FIG. 4 is a perspective view of a valve-spring mechanism.

Additionally, although described as springs or spring elements, it is to be appreciated that the valve assembly/mechanism 109 shown in FIG. 1a may include any resilient member or element that can deflect, depress, compress, or otherwise move to open the valve membrane 110. For example, FIG. 4 shows the valve unit 109 separated from the port 100. The valve unit 109 includes a membrane 110 connected to a base 107 by a plurality of resilient elements or members 104. Any suitable number of resilient members or elements may be used to separate the membrane 110 from the base 107. For example, a single resilient element may be connected at the centers of the membrane 110 and the base 107 where the base 107 may include one or more orifices around the outside of the resilient element to allow fluid to pass through the base 107 to the outlet. Also, as shown, the resilient members 104 are interposed between the membrane 110 and the base 107; however, the resilient element(s) may be placed at any suitable location in the valve assembly to facilitate the opening and closing of the valve.

Referring again to FIGS. 1a and 4, the resilient members are capable of moving between a relaxed resting state and a deflected state. In the resting state, the valve assembly 109 is closed to prevent fluid flow. To move the resilient members 104 to a deflected state, the membrane 110 can be pushed toward the base 107. This reduces the distance R between the membrane 110 and the base 107. In order to accommodate the reduced spacing R, the resilient member/element can compress, bend, or depress. While the resilient members are deflected, the valve unit 109 is open.

In some embodiments, the resilient members/elements are made from silicone and formed into thin resilient struts. In other embodiments, the resilient members/elements can be made from any suitable materials including coiled or uncoiled thin metal wire. Any biocompatible material can be used, including elastomeric polymers, that can bend, compress, depress, or otherwise deflect from force or pressure imparted by a delivery device such as an enteral syringe.

Figure 3:
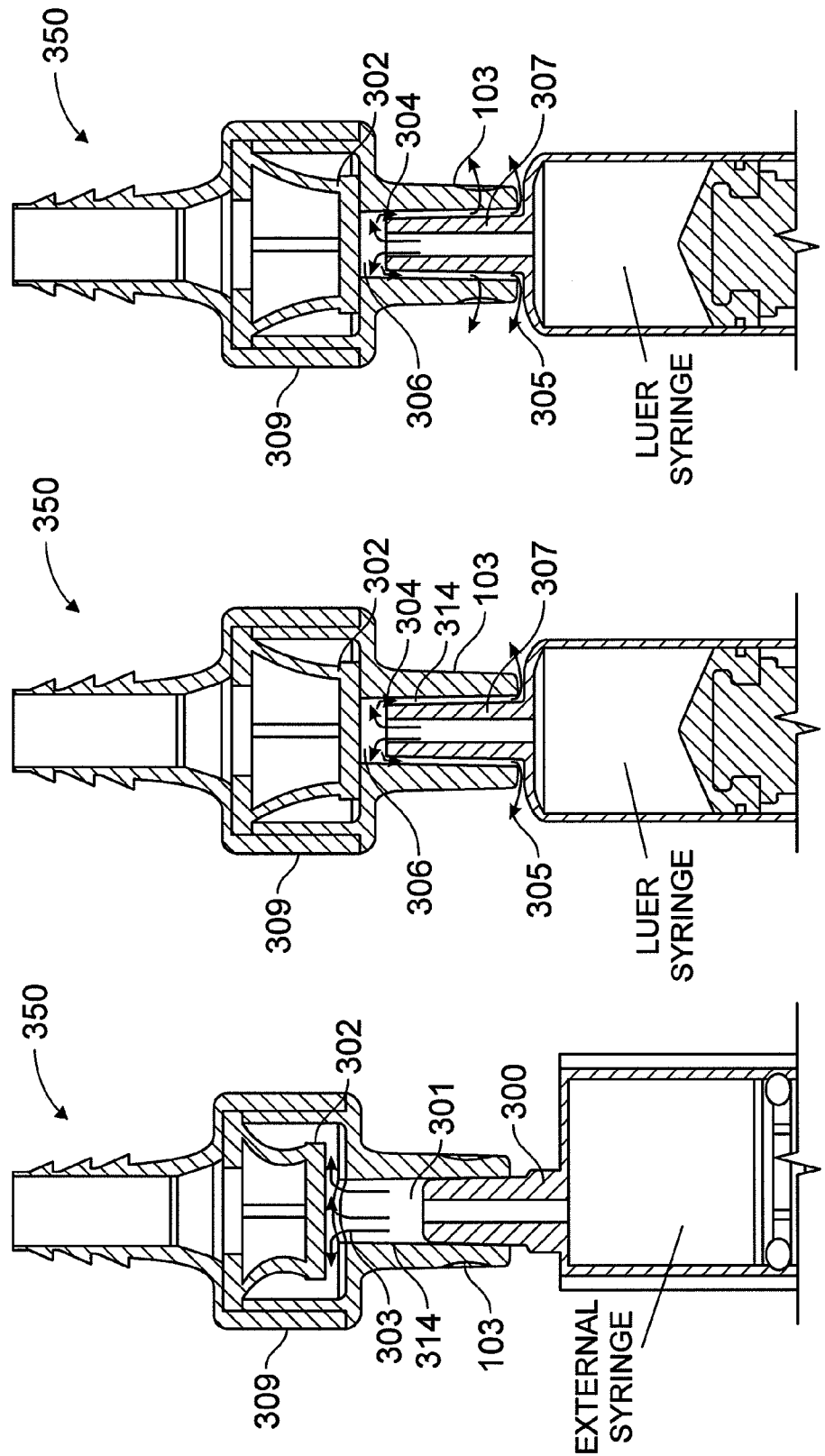
FIG. 3a illustrates a sealed connection between an enteral syringe and an enteral administration port to allow fluid pressure to open a valve.
FIG. 3b illustrates how a luer syringe does not form a seal and fluid leaks out of the inlet, unable to create pressure to open the valve.
FIG. 3c shows an embodiment having slits in the inlet of the port to enhance the leak path and ensure insufficient pressure to open the valve when the port is coupled to a luer syringe.

Advantageously, some embodiments provide for an enteral administration assembly or port that cannot form a sealed connection with a luer-type device. This prevents unwanted misadministration of enteral-destined-substances into other ports. FIGS. 3a-3c show a comparison between an enteral syringe and a luer syringe when each is separately inserted into the inlet 301 of exemplary enteral administration assembly/port embodiment 350. FIG. 3a shows the enteral syringe tip 300 matingly fitted into the lumen 314 of the inlet 301. The dimensions of the lumen 314 are sized and configured to correspond with the dimensions of the enteral syringe tip 300. The inner diameter of the lumen 314 may be designed to taper or decrease in diameter along a length of the inlet 301. Additionally, the width or diameter of the lumen 314 may be sized to accommodate the enteral syringe tip 300 through a portion of but not the entirety of the lumen 314. For example, the lumen 314 may include a section where the width or inner diameter is smaller than the smallest diameter of the syringe tip 300. Thus, the tip 300 can only be inserted partially into the lumen 314. In other embodiments, the enteral tip 300 can be inserted completely into the lumen 314.

In further embodiments, the inlet may include a hole or slit 103. The slits or holes provide an additional safeguard against the misconnection of a non-enteral device to the port 350. Referring to FIG. 3*a*, in some embodiments, a tight seal between the enteral syringe tip (300) and the inlet 301 occurs distal to the open slits (103). In such variations, no fluid can escape through the open slits 103 as the seal connection is formed distal of the slits 103 and toward the inner lumen opening near the valve 302. When fluid is transferred from the syringe tip 300 to the port 350, the positive pressure of the fluid opens the valve (302) and fluid 303 flows into the valve assembly (309).

FIG. 3*b* illustrates how the dimensions and taper of an enteral administration assembly or port do not allow a sealed connection with a luer tipped syringe. In FIG. 3*b*, the tip (307) of a luer type syringe is in the port inlet 301. However, a seal is not formed as unsealed space (304) exists between the luer tip 307 and the inner surface of the lumen 314. Fluid leaks out of the base 305 of the inlet 301. As such, there is not sufficient positive pressure to open the valve 302. The valve 302 remains shut (306) and fluid cannot enter the area within the valve assembly 309 or flow through the port 350.

FIG. 3*c* illustrates an additional (but optional) safety utility of the embodiment. In the event a user presses a luer tipped syringe or other undersized connector hard against the port, the inlet wall has open slits (103) which serve to ensure that the valve does not open. Only an enteral connector/tip/device will form a snug mated fit at the inlet wall to provide an air and fluid seal. Any fluids or gases injected into the inlet without such a seal will leak out of the slits and not go through the valve 302. No pressure gradient will build within the inlet, and the valve will not open. These sidewall slits could also protect against any accidental misconnection of suction machines, or medical gas delivery devices, which has unfortunately happened in the past.

Additionally, because some luer tip syringes come without screw locking tips, some embodiments include an enteral administration assembly as described having a one-way valve to provide additional protection against withdrawing a fluid volume through an enteral device out of the patient.

In operation, embodiments of the enteral administration assembly or port can be attached to one or more enteral-type devices. In such variations, the enteral administration assembly can couple to a first enteral device at one end and a second enteral device at the other end. Referring to FIGS. 1*a*-1*b*, the outlet 105 may be removably or permanently attached to an enteral fluid delivery device (e.g. GI-tube or rectal tube) that partially resides in the patient's body. The outlet 105 may be mechanically connected to the lumen of the enteral fluid delivery device directly or indirectly through adaptors or connectors.

Additionally, the enteral administration assembly or port can be attached to an enteral-type device such as an enteral tapered syringe at the inlet of the port. As shown in FIG. 3*a*, the tip of the enteral tapered syringe mates with the inlet 301 to form a sealed connection allowing fluid flow from the syringe through the enteral administration assembly 350. The injected fluid can exit the assembly 350 through the outlet and enter an enteral device, such as a connected enteral tube. Advantageously, the inlet can be designed to couple only to certain types of enteral devices such as enteral connectors or enteral tapered syringes, which prevents misadministration of medication to the patient.

As mentioned, in another aspect, embodiments described provide for enteral administration systems, assemblies, or ports that produce turbulent fluid flow. Referring again to FIG. 4, the valve mechanism 200 includes a valve membrane 110, a base 107, and resilient members 104. In some embodiments, components of the valve mechanism (e.g. membrane 110, base 107, and resilient members 104) can also serve as turbulators within the valve housing, keeping particles in suspension by creating eddies in the flow within the housing.

FIGS. 5*a*-5*c* illustrate this phenomenon in more detail. FIGS. 5*a*-5*b* show a two dimensional schematic of laminar flow becoming turbulent when encountering an obstacle. As fluid flows by obstacle 1504, the laminar flow 1501 is disrupted into a turbulent flow 1502. FIG. 5*c* shows fluid flow through the enteral administration port 1550. The port 550 is coupled to a syringe 1552. When the syringe 1552 injects fluid into the port 1550, the injected fluid exhibits a laminar flow in the inlet of the port 1550. Laminar flow 1501, depicted by straight black lines within the tip of the syringe enters the valve assembly 1554. Once the fluid flows into the valve assembly 1554, the fluid encounters a turbulator 1556, which disrupts the laminar flow 1501 and causes turbulent flow 1502. Turbulent flow, as depicted by curved black lines (1502), is produced by the fluid hitting a number of obstacles which can create eddies in the current or change the direction of flow, increasing the overall kinetic energy of the flow and causing turbulence. Once the fluid exits the valve assembly 1554, the flow may return to laminar flow 1501. Alternatively, the port may be designed with turbulators that produce or maintain turbulent fluid flow through the port and into the lumen of a receiving device such as a gastro-intestinal feeding tube.

In some embodiments, the valve assembly may include one or more turbulators. In some cases, the valve assembly components such as the valve membrane, base, and/or resilient members/elements can serve as obstacles to fluid flow for producing turbulence. As such, the valve components may serve the dual purpose of controlling fluid flow through the port and producing turbulence.

In other embodiments, the diameter or width of the interior of the enteral administration port or assembly is configured to promote or facilitate turbulence within the valve housing. One way to achieve this is by setting the dimensions of the port such that fluid channels or passageways within the port are greater than the dimensions of a syringe or other device that is used to introduce the fluid into the port. For example, referring to FIG. 7, the interior dimension of any channels formed by the port 1000 in the open position, including the outlet orifice (1004), is larger than the diameter d1 of the opening of an enteral syringe tip 1001. As shown, the port valve 1008 is open which allows fluid to pass from the syringe tip opening into the valve assembly 1010. While the fluid passes through the lumen of the syringe tip 1001, fluid flow is constrained by the boundaries and dimensions of the syringe tip. Once through the syringe tip opening and into the valve assembly 1010, the fluid is no longer contained by the smaller space in the syringe tip 1001. The increased space and volume of the valve assembly 1010 facilitates turbulent flow so that clogging of large particulates cannot occur.

Figure 7:
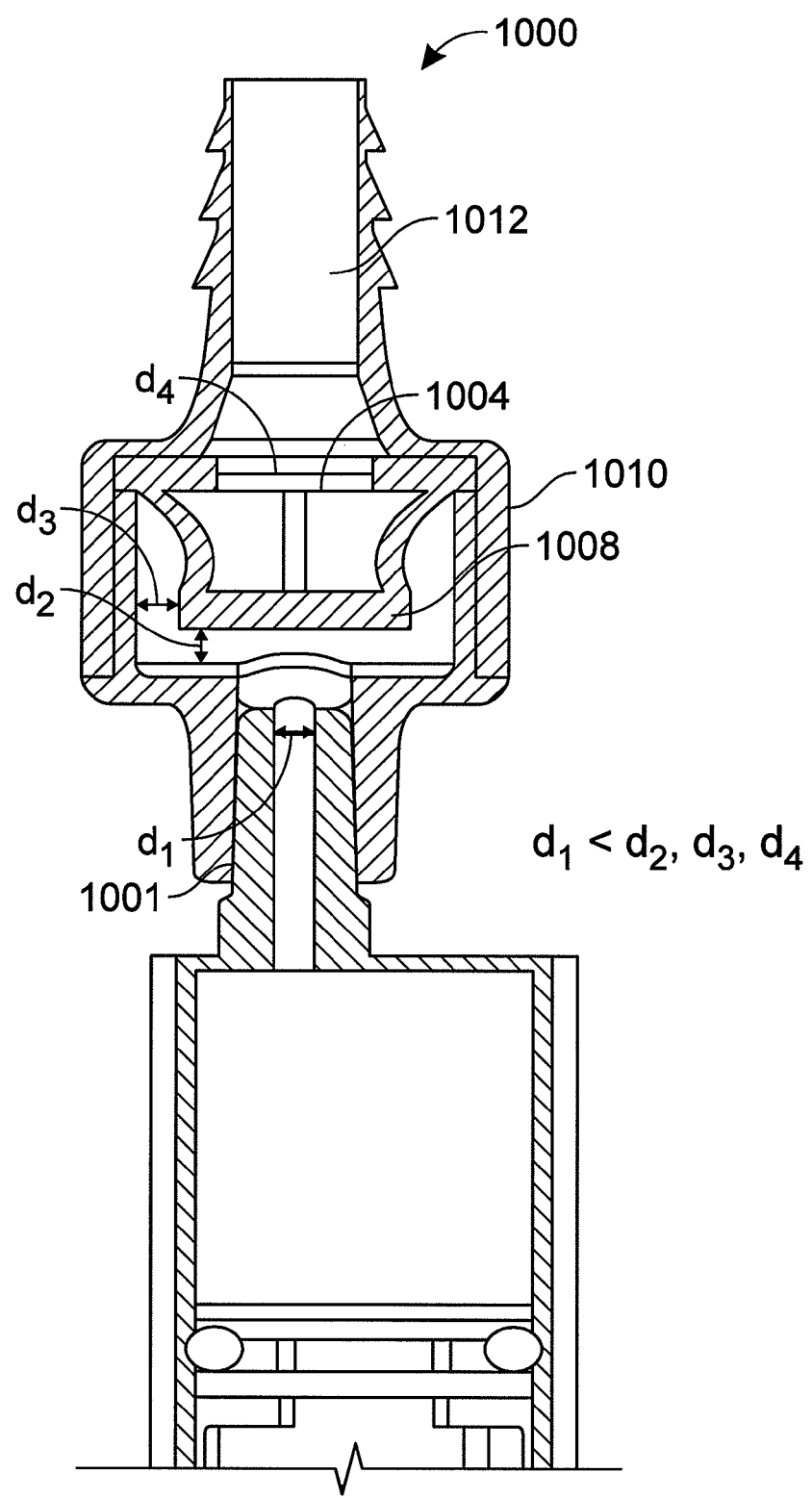
FIG. 7 illustrates the dimensions of the smallest areas within the valve housing are larger than that of the enteral device tip, where ($d_1$) is the diameter of the enteral device tip and $d_2$, $d_3$, and $d_4$, are dimensions of the three smallest portions of the valve through which fluid flows.

In particular, FIG. 7 shows the dimensions of different areas within the valve housing that are larger (e.g. wider) than that of the enteral tip, where (d1) is the diameter of the enteral tip 1001 and d2, d3, and d4, are dimensions of the three smallest portions of the valve assembly 1010. In some embodiments, the smallest portions of the valve assembly are greater than or equal to the diameter d1. In other embodiments, the width, area, spacing, or volume within the fluid pathways of the valve assembly are greater than the diameter of the syringe tip opening. Additionally, the dimensions of the outlet section 1012 of the port 1000 can also be designed to promote turbulent fluid flow. In some embodiments, the diameter or width of the outlet section 1012 (including outlet opening 1004) may be larger than the syringe tip opening.

In further embodiments, additional turbulators or flow obstacles may be placed along the fluid flow-through path in the port. For example, turbulators may be placed in the inlet or outlet to maintain suspended particles during delivery through the port.

Figure 8B:
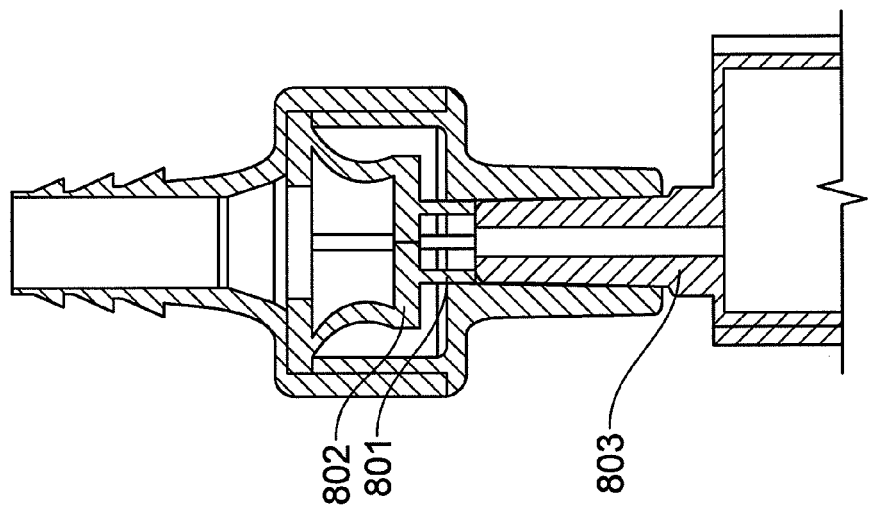
FIGS. 8a-8b illustrate one embodiment of a bi-directional flow valve.
Figure 8A:
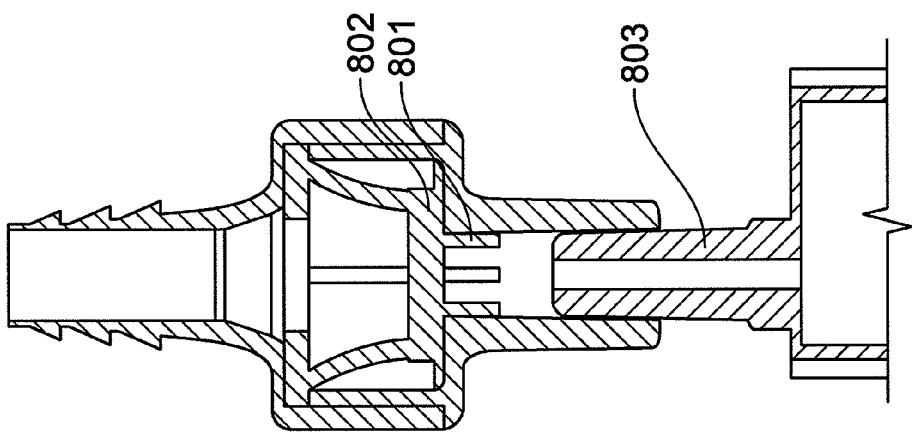

In other embodiments, it may be beneficial to allow for two way or bi-directional flow. For example, bi-direction flow allows for extraction of a sample from the lumen or to enable positive/negative pressure cycles to try to dislodge a clog in the lumen. FIGS. 8a-8b show an enteral administration assembly having a valve mechanism similar to that of the embodiment of FIGS. 1a-1b, but with valve opening elements or small prongs/tines (801) on the outer surface of the valve membrane. These opening elements 801 can interface with the tip of an enteral syringe (803) to push the valve (802) into the open position. When the enteral syringe is not inserted or attached, the valve remains closed. When the enteral syringe is pushed in place, the valve is opened and fluid can be pushed into and withdrawn from the valve by the syringe. Although shown as having multiple opening elements 801, one or more opening elements may be used.

Figure 6:
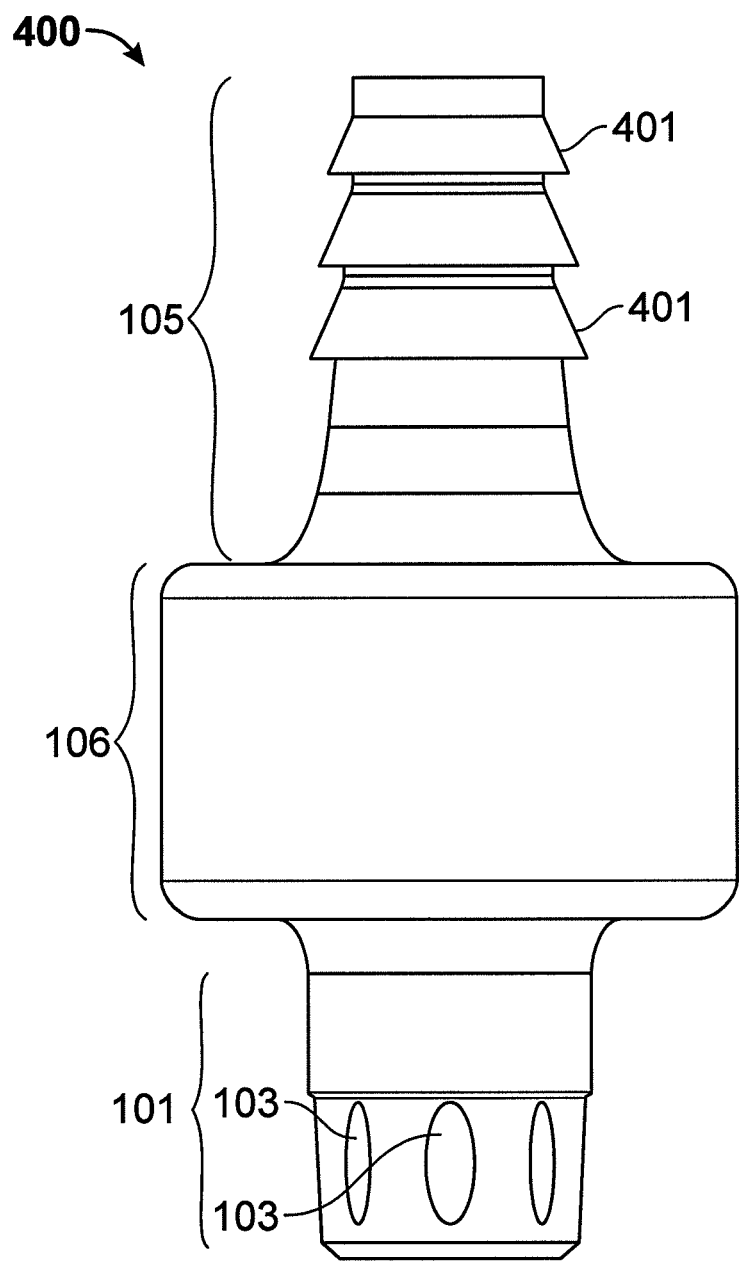
FIG. 6 provides a side view of an enteral administration assembly body.

Additionally, FIG. 6 shows another embodiment of the enteral administration assembly or port. The port body (400) could be made from one of many forms of hard plastic. In this embodiment it has three distinct units: the inlet (101), the outlet (105), and the valve housing (106). In the present embodiment the outlet can contain barbs (401) or other mechanical locking features so it can be easily, yet permanently attached to a mating enteral medication administration lumen during fabrication. Alternately, the port exit body could be made without mechanical locking features and secured with adhesive to a lumen of the medication delivery device. The slits on the inlet are also visible in this diagram.

Figure 9:
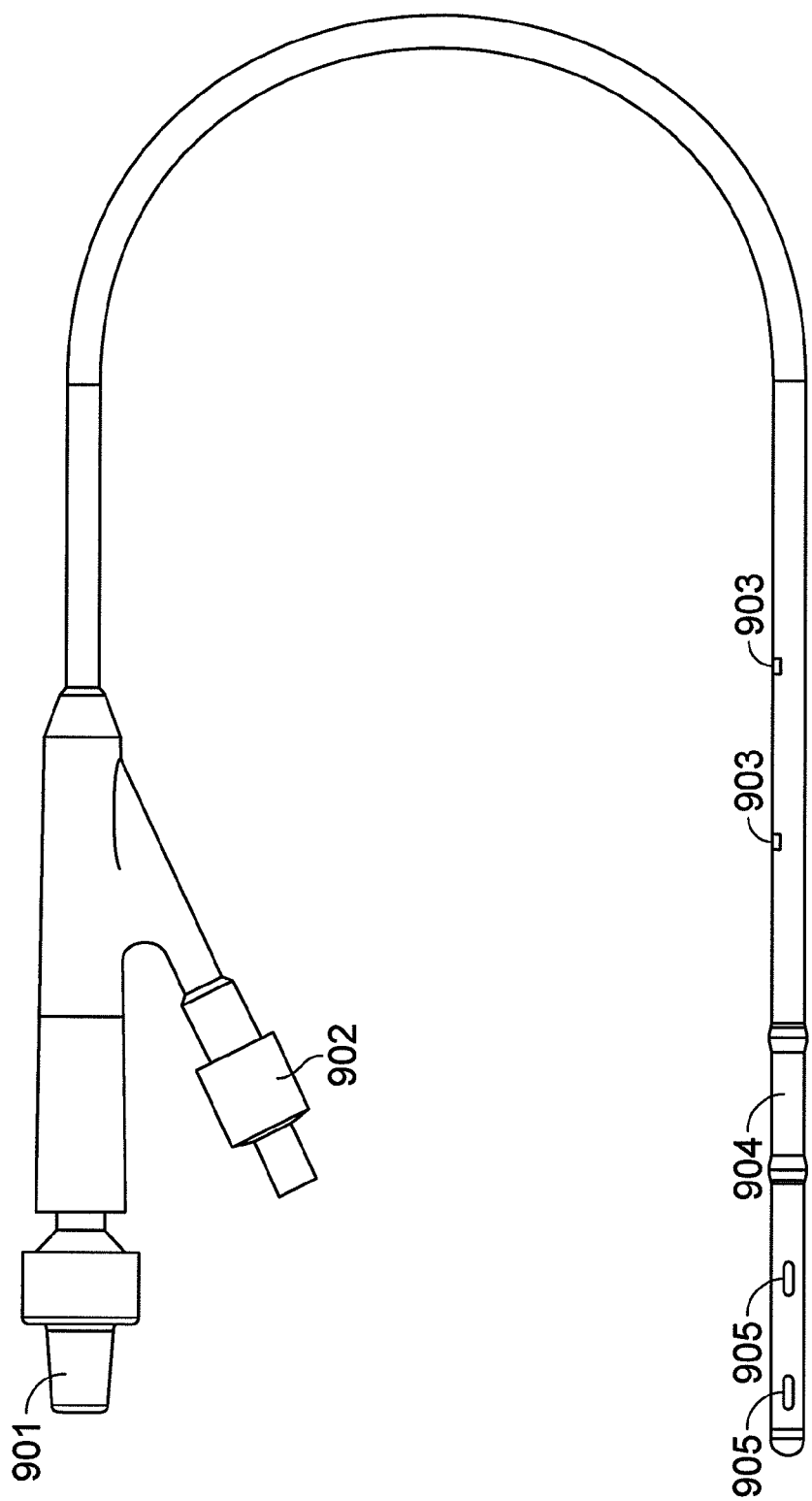
FIG. 9 illustrates an improved rectal medication administration device wherein an enteral administration assembly according to described embodiments is permanently attached to the device.

FIG. 9 is an illustration of a rectal medication administration device with a valved enteral administration assembly or port (901) permanently attached to the end. This device can be inserted into the rectum, the balloon (904) inflated at the balloon inflation port (902), and medications can safely be administered into the device through the valved port 901 and into the rectum via transmission holes (905) without the concern of injury due to misconnection of luer devices, oxygen or other medical gasses, or suction machines to the device. In addition, because medications for this device must be drawn into enteral syringes, it would mitigate the risk of critical errors caused by enteral medications being given to patients intravenously.

Figure 10:
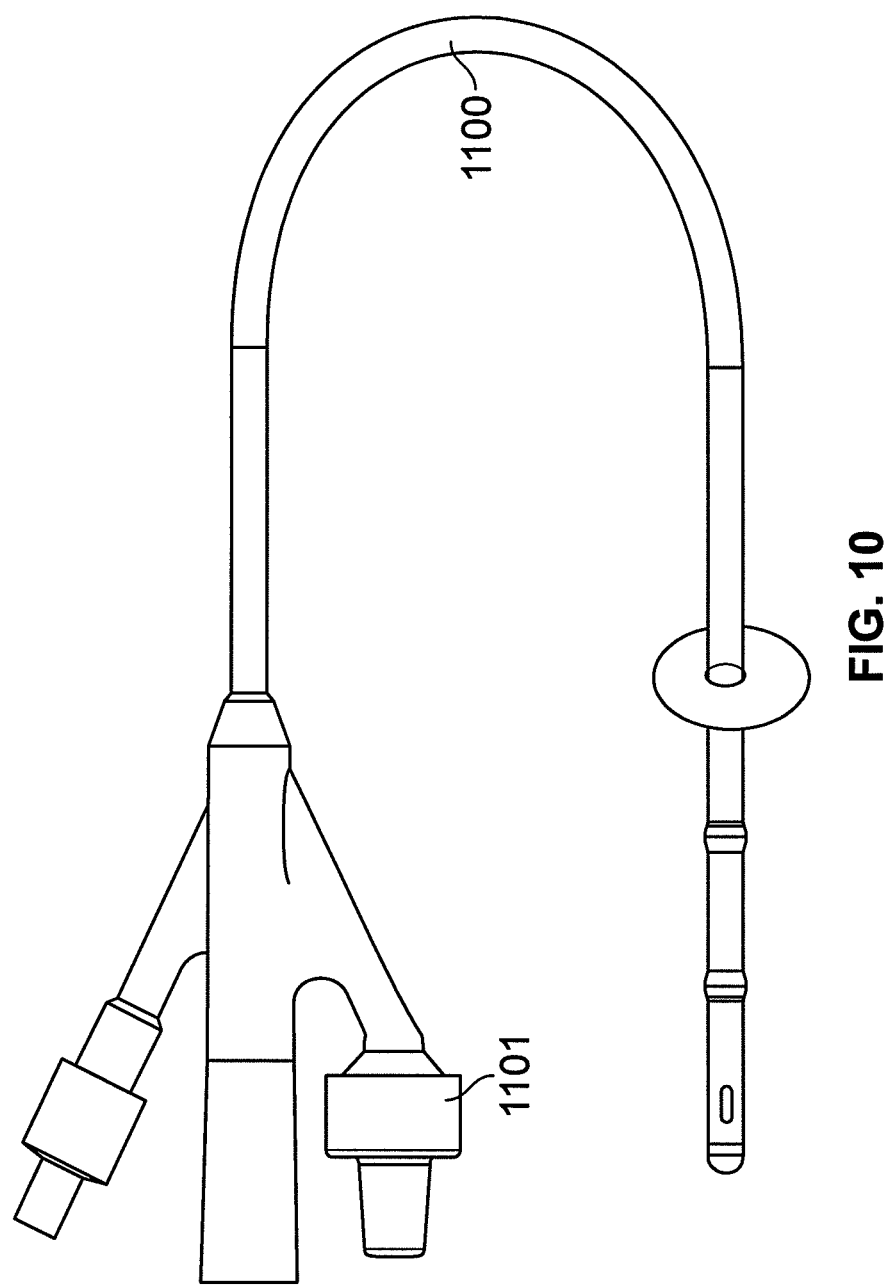
FIG. 10 illustrates of an improved gastro-intestinal tube having an enteral administration assembly according to described embodiments attached to the side port.

FIG. 10 is an illustration of a g-tube (1100). The figure illustrates how this gastric tube, or any other tube which delivers medication to the gastro-intestinal tract can be improved with the addition of the valved enteral administration assembly (1101) of the present invention. By placing said valved assembly on the medication side port of these devices, medications can be given without leakage of feedings, medications, or gastro-intestinal contents out of the patient, contaminating the environment. Medications can safely be administered into the device through the valved assembly 1101 without the concern of injury due to misconnection of luer devices, oxygen or other medical gasses, or suction machines to the device. In addition, because medications for this device must be drawn into enteral syringes, it would mitigate the risk of critical errors caused by enteral medications being given to patients intravenously.

Figure 11:
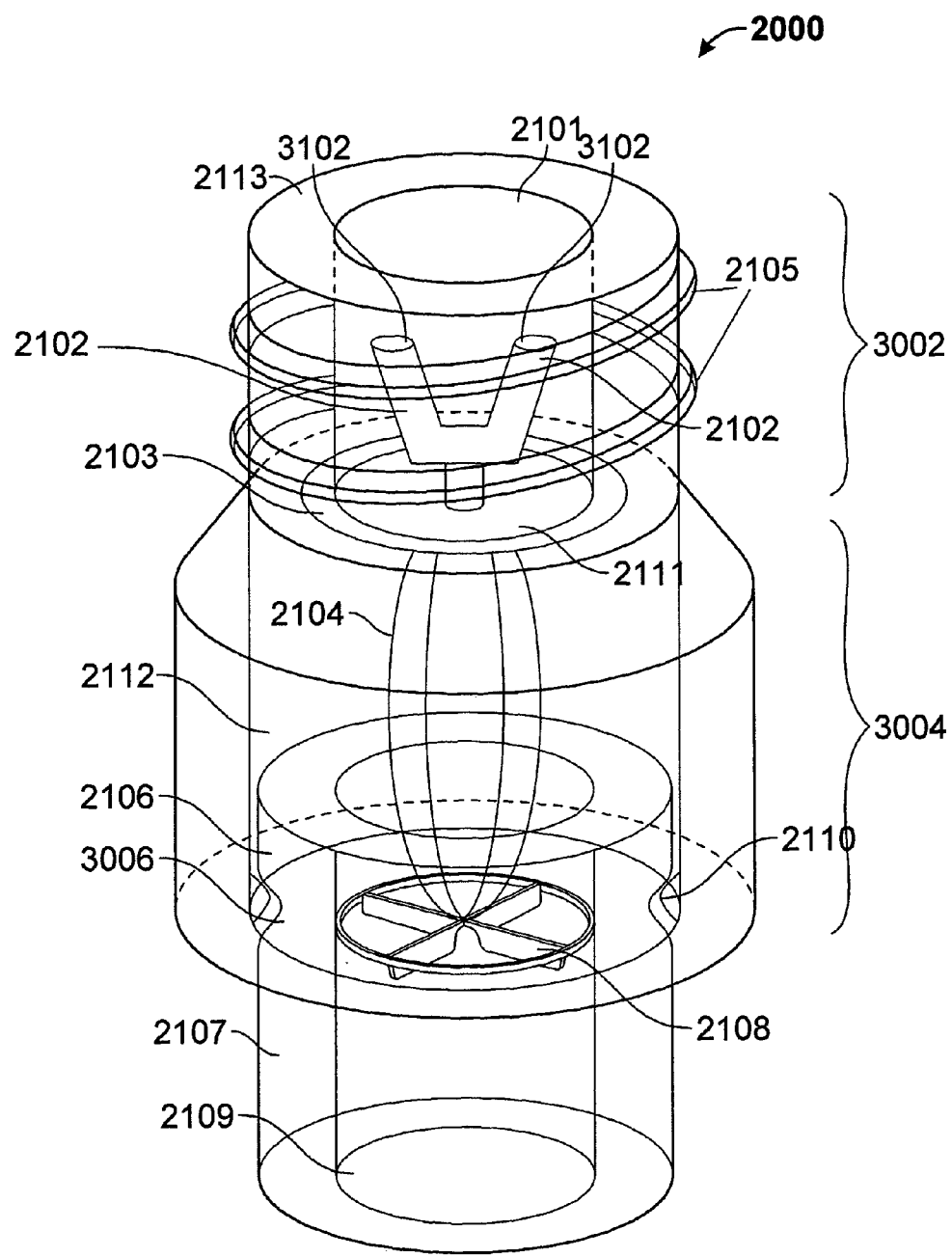
FIG. 11 is an illustration of a fluid delivery device having a turbulent flow valve assembly in which the valve is closed. No syringe or other similar device is attached and the valve is shut.

In another aspect, embodiments contemplated provide for a turbulent flow valve or valve system that can be used with enteral administration assemblies/ports or other fluid transfer devices. FIG. 11 is an illustration of a fluid delivery port 2000, such as an enteral administration port/assembly, which includes a turbulent flow valve mechanism that can be used with medical devices in which fluids in suspension are administered to a body cavity. As shown, the assembly 2000 is made of two units which fit together and connect to a fluid transfer tube (2107). These two units are defined as a housing body (2113) and a turbulating mechanism (2300). The housing body (2113) could be made of any suitable moldable material such as inelastic, rigid, or hard plastic. The turbulating mechanism could be made completely or partially of a softer more pliable, elastic, or compliant material such as a flexible plastic.

As show, the housing body 2113 has two openings on opposite ends. In particular, the housing body 2113 has a first opening or orifice 3006 and a second opening or orifice 2101. A tubular lumen extends between the two openings. In some embodiments, a portion of the housing body 2113 near or about the first opening 3006 is designed to interface and couple to a fluid transfer or transmission device. For example, a distal end of the housing body may be designed to interface and couple with a syringe tip. In other embodiments, a portion of the housing body 2113 near the first opening 3006 is configured to interface with a lumen of a fluid delivery device such as the lumen of an enteral feeding tube. Additionally, the inner surface of wall of the housing body 2113 may include mechanical features or surface features to facilitate the locking or coupling between the administration assembly 2000 and a fluid transfer tube 2107. For example, grooves, wedges, protrusions, grips, barbs, etc. may be used hold the fluid transfer tube 2107 inside the assembly 2000.

As shown, the housing body 2113 includes a second opening or orifice (2101) which is designed to accept the tip of any typical medical syringe or intravenous tubing. The external distal surface has screw grooves (2105) to accept and attach a luer locking syringe. Alternatively, the second opening or orifice 2101 may be designed to restrictively engage and accept specific compatible devices. In such variations, the second opening 2101 may be configured to only couple to enteral-type devices such as enteral connectors or enteral tapered syringes. As shown in FIG. 11, the orifice (2101) has an additional opening (2111) which leads into a valve chamber (2112).

In some embodiments, the housing body 2113 includes two or more sections of varying dimensions. For example, referring to FIG. 11, the housing body 2113 is formed from a hollow tube with a first section 3002 having a smaller outer width or diameter compared to a second section 3004. The inner diameter or width of the tube may be the same or different along the length of the housing body. In some embodiments, varying dimensions between the housing body sections allow for a valve to interface with different fluid transfer devices at different openings or ends. In other embodiments, the varying dimensions allow the valve to be opened by moving the valve to a portion of the housing body with a greater diameter. For example, in the closed state, the valve may sit in a portion of the housing body where the valve diameter is the same or smaller than the diameter of the surrounding body. To open the valve, the valve is pushed or moved into another portion of the housing body with a larger diameter, a vacant space is then created around the valve to facilitate fluid to flow past the valve.

Referring to FIGS. 11-13b, a turbulating or valve mechanism 2300 may be positioned inside the housing body 2113, such as within the orifice 2101. As shown, the turbulating mechanism 2300 includes a first turbulator 2102 having a fork, Y or V-shaped knob with protruding prongs. The fork-shaped knob turbulator 2102 is attached to a valve member or membrane 2103. In some cases, the fork-shaped turbulator 2102 is attached to the valve member 2103 by way of an elongated member 3106 shown in FIGS. 13a-13b.

In other embodiments, the first turbulator is also a valve opening element. The first turbulator 2102 may include one or more prongs or features that can serve as valve opening elements 3102 for opening the valve member 2103. For example, FIGS. 11-13b show a knobbed turbulator 2102 with opening elements or prongs 3102 that can be used to move, depress or deflect the valve member 2103 to an open position.

In some embodiments, the valve member is a circular shaped membrane separating an inlet portion 3002 from the rest of the device 2000. Moreover, the valve member 2103 can also serve as a turbulator.

The valve membrane 2103 can be attached to a second turbulator 2104. In some embodiments, the second turbulator 2104 is a compression spring formed from a plurality of thin resilient members 3100. The thin resilient members 3100 may be attached to a side of the valve membrane 2103 opposite the attachment site of first turbulator to the valve membrane 2103. In some cases, the spring 2104 is formed from a biocompatible material such as silicone or nitinol. In further embodiments, the second turbulator 2104 can be any resilient or non-resilient member that produces a turbulent fluid flow.

Additionally, the second turbulator 2104 may be attached to an anchoring support member 2108. FIGS. 13a-13b show the anchoring member 2108 having a circular frame 3108 and a plurality of struts 3110 radially extending from a center to the periphery of the frame. The struts are connected to the ends of the thin members 3100 of the second turbulator 2104. As shown, the ends of the thin members 3100 distal from the valve membrane 2103 are attached to strut ends located near or at the center of the anchoring member 2108. In some embodiments, the anchoring member 2108 also serves as a turbulator.

For easy reference purposes, the first turbulator 2102, valve member 2103, spring 2104, and anchoring member 2108 may be referred collectively as the turbulating or valve mechanism. It is to be appreciated that the phrase turbulating or valve mechanism is not limiting the invention to these components and that the contemplated embodiments can include additional or fewer of the described features.

Referring again to FIG. 11, when no syringe is attached, the valve membrane (2103) is closed against the opening (2111) by tension from the spring (2104). The fluid delivery assembly 2000 is connected to the fluid transmission tube (2107) by being squeezed or compressed between the base of the turbulating mechanism and wedges (2110) in the inner wall of the valve housing body (2113) at (2106) on FIG. 11. As shown, the anchoring support member 2108 is configured to be placed inside the fluid transmission tube 2107 (e.g. in an orifice or lumen 2109 of the tube). The circular frame 3108 provides structural support inside the tube to oppose a compression force exerted by the inner wall of the housing body 2113 against the outside of the tube 2107. This allows the tube 2107 to be fixed or attached to the fluid delivery assembly 2000 by holding or pinching the wall of tube 2107 between the housing body 2113 and the anchoring member 2108. The inner wall of the housing body 2113 may include mechanical or surface features to facilitate this attachment.

Figure 12:
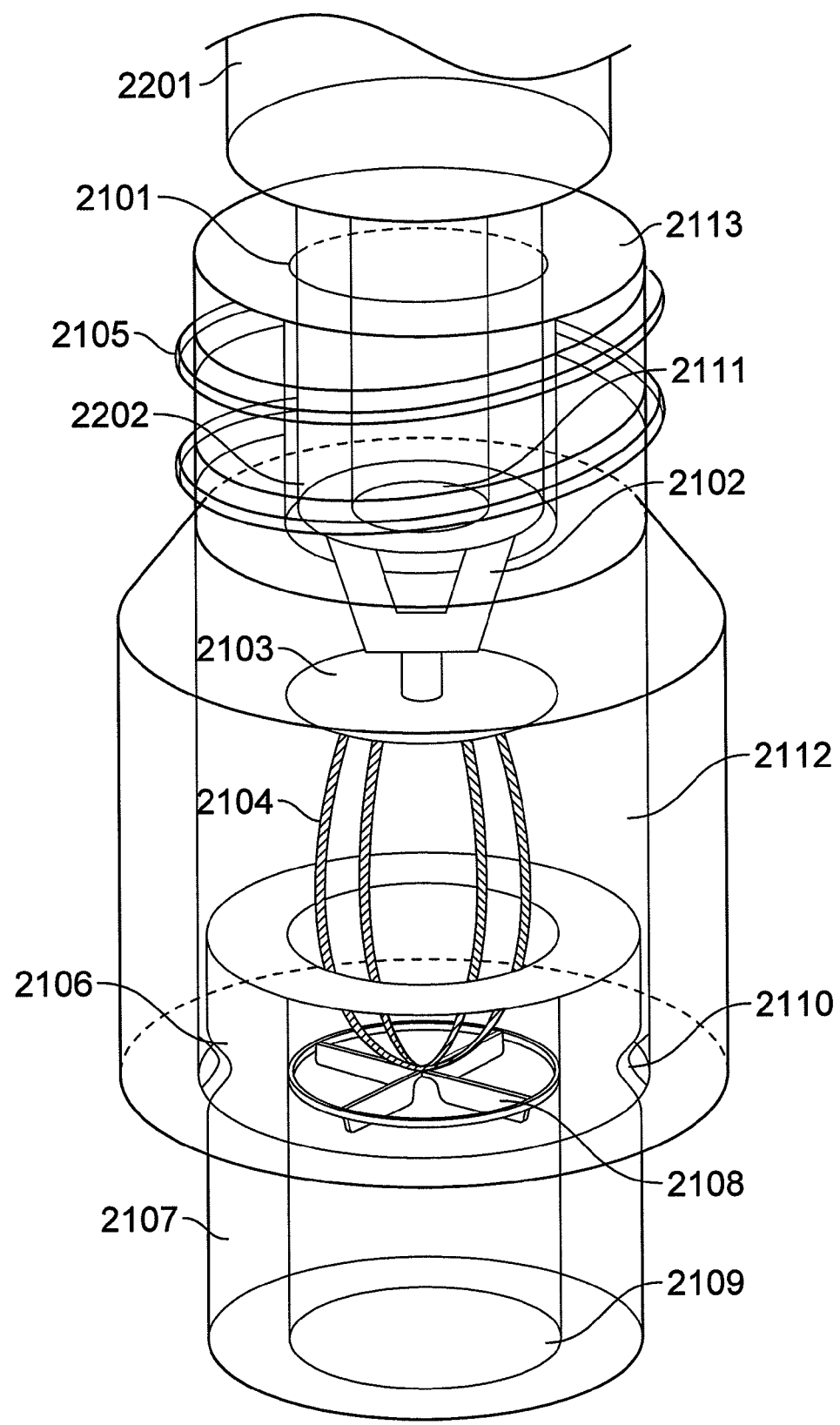
FIG. 12 is an illustration of a turbulent flow valve assembly in which the valve is open. The tip of a syringe is attached to the proximal end of the valve pushing on a knob-valve-spring turbulating mechanism, which opens a valve allowing fluid to be injected into the valve.
Figure 13:
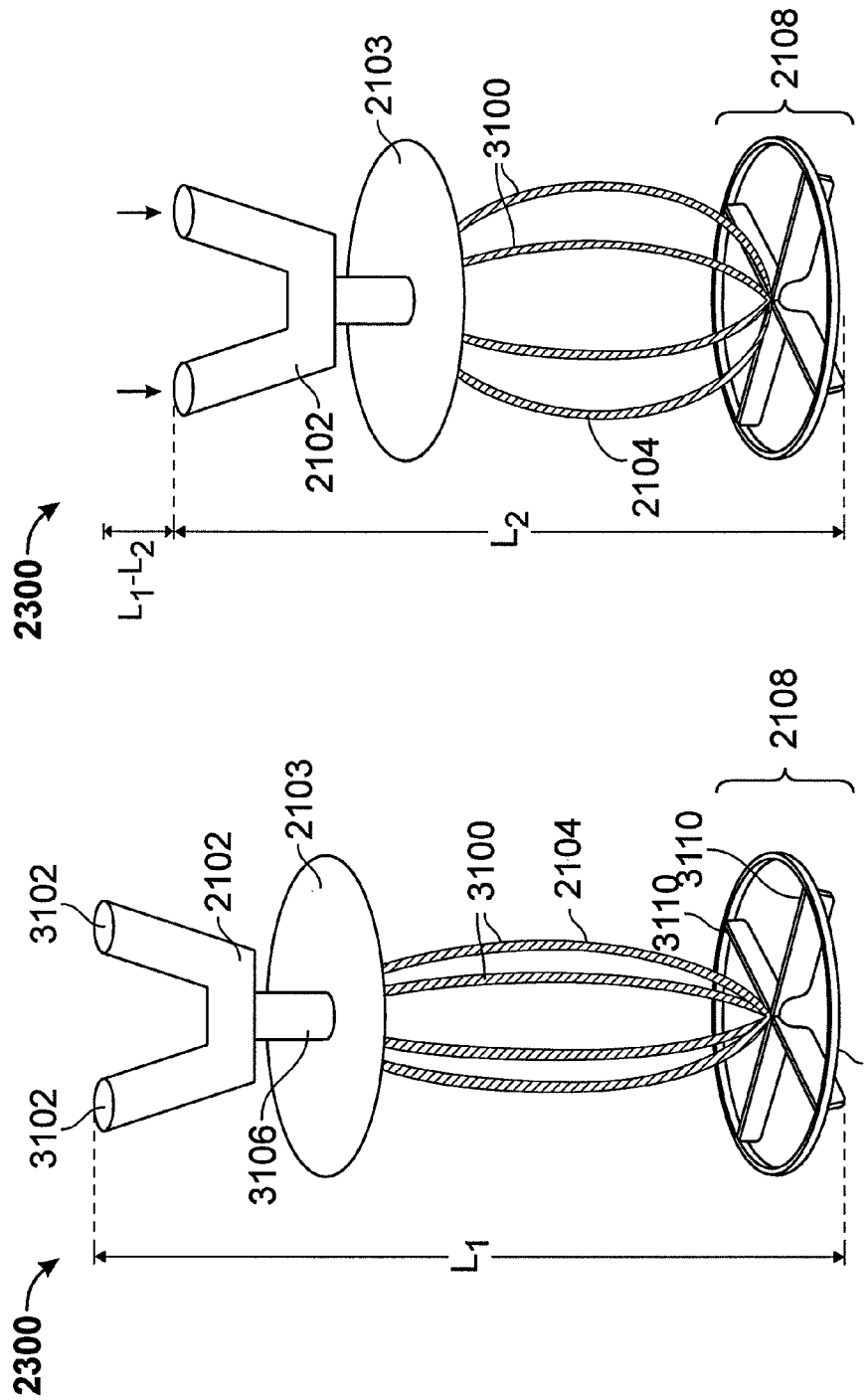
FIGS. 13a-13b show a knob-valve-spring turbulating mechanism with no tension and with tension applied respectively.

Once attached to the fluid transmission tube 2107, the fluid delivery device 2000 may be used to transport or deliver fluids to a patient. FIG. 12 illustrates the open clog resistant device 2000 of FIG. 11 in an open configuration. The device 2000 is connected to a fluid transmission tube 2107 and a syringe 2201. When a syringe (2201) (or intravenous tubing) is inserted into the orifice (2101), the tip of the syringe (2202) presses against knob or valve opening element (2102). The force applied by the syringe tip against the knob 2102 also presses against the valve membrane 2103. Once pressed, the valve membrane 2103 also imparts or transfers the force to the spring (2104) which causes deformation, deflection, compression, and/or depression of the spring 2104. When the syringe 2202 is removed, the spring 2104 returns to its resting state, and the valve membrane 2103 closes again, allowing fluid to remain in the device 2000 and tube, without leaking out.

FIGS. 13a-13b show the turbulating or valve mechanism (2300) in both a resting and deflected/compressed state. In the compressed state, the spring 2104 is deformed as a force is applied to the knob 2102. FIG. 13b shows how the length of the mechanism changes in the compressed state. The length of the mechanism is indicated by (L). (L1) is the length of the turbulating mechanism (2300) in the resting state of the spring with the valve closed. (L2) is the length of the turbulating mechanism (2300) when a force is applied to the knob (2102). The change in length of the mechanism (2300) opens and closes the valve membrane 2103.

In further embodiments, turbulating mechanism (2300) serves a second function other than opening and closing the valve. It is designed to create obstacles (turbulators) which transition laminar flow to turbulent flow by creating eddies and changes in the vector of fluid flow through the valve. An eddy is the swirling of a fluid and the reverse current that is created when the fluid flows past an obstacle. Eddies and vortices produced by obstacles within the path of flowing fluid cause increases in the kinetic component of the flow as described in the summary above.

Figure 14:
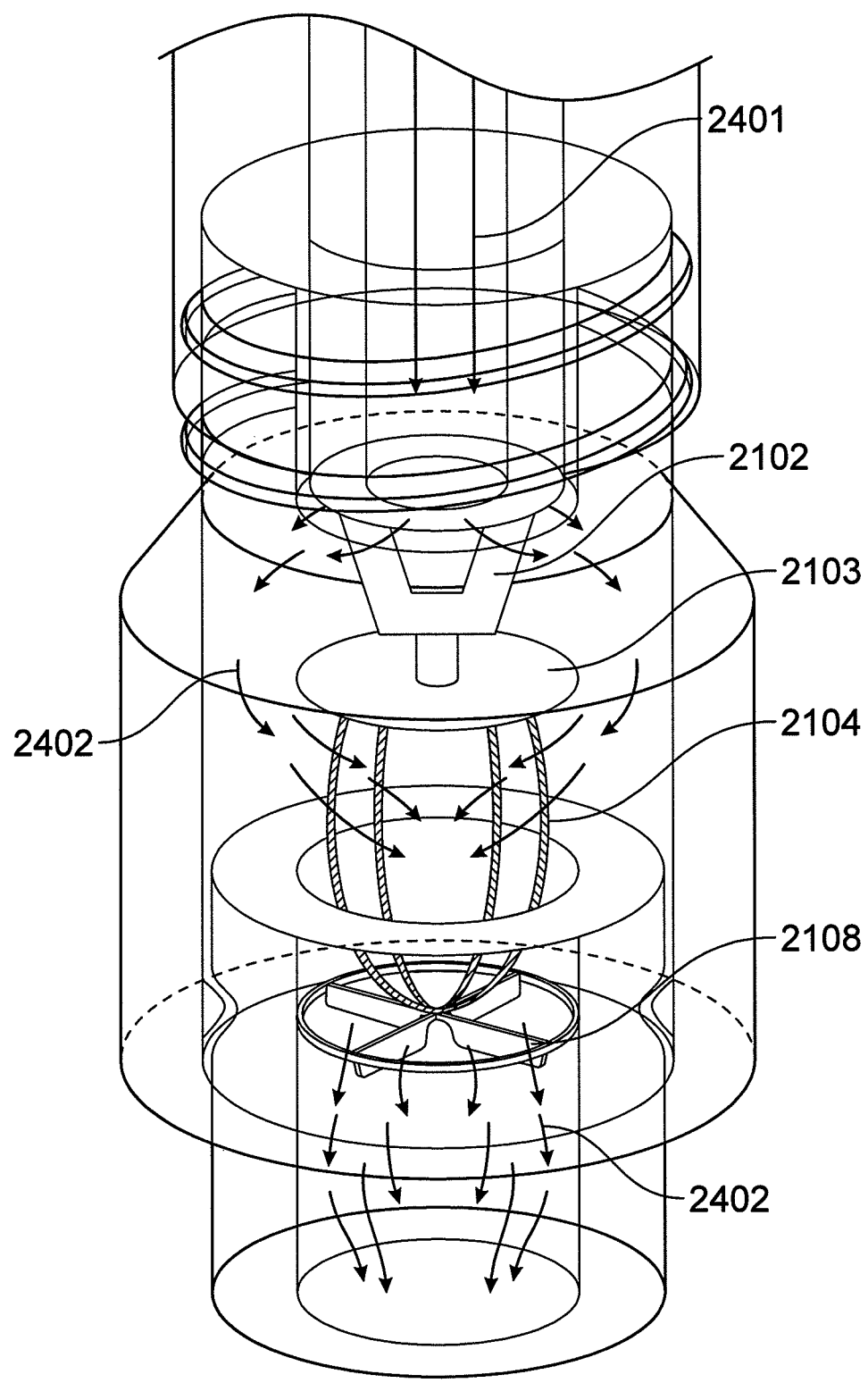
FIG. 14 illustrates a fluid delivery device with a turbulent flow valve mechanism. Fluid turbulence is shown generated within the valve mechanism by the fluid hitting obstacles (turbulators) which increase the inertial force component within the fluid.

FIG. 14 shows fluid flow through the turbulent flow valve and the creation of turbulent flow when the fluids pass through these obstacles. Laminar flow, depicted by thicker black lines (2401) enters the valve from the syringe. It is transformed into turbulent flow, as depicted by smaller black lines (2402) by hitting a number of obstacles known as turbulators which create eddies and vortices in the current through the valve, or change the direction of flow causing turbulence. The first obstacle is the forked shaped knob turbulator (2102) which creates an eddy as fluid flows by it. Next, the circular valve (2103) creates a change in the vector of the flow as fluid hits it and must change course to go around it. Next, the fluid passes the compression spring turbulator (2104) which creates eddies. Lastly it passes through the anchoring support turbulator (2108) which again creates eddies as the fluid passes by it producing turbulent flow as the fluid enters the fluid transmission tube. In some embodiments the anchoring support turbulator may be designed to create a vortex by spinning the fluid in one direction.

FIGS. 15a-15b show a two dimensional schematic of laminar flow becoming turbulent when encountering an obstacle. FIG. 15a shows flow changes creating turbulence, in general, as they would occur around obstacles (2102, 2104 and 2108), and FIG. 15b depicts flow changes, in general, creating turbulence caused by obstacles (e.g. 2103).

Figure 16:
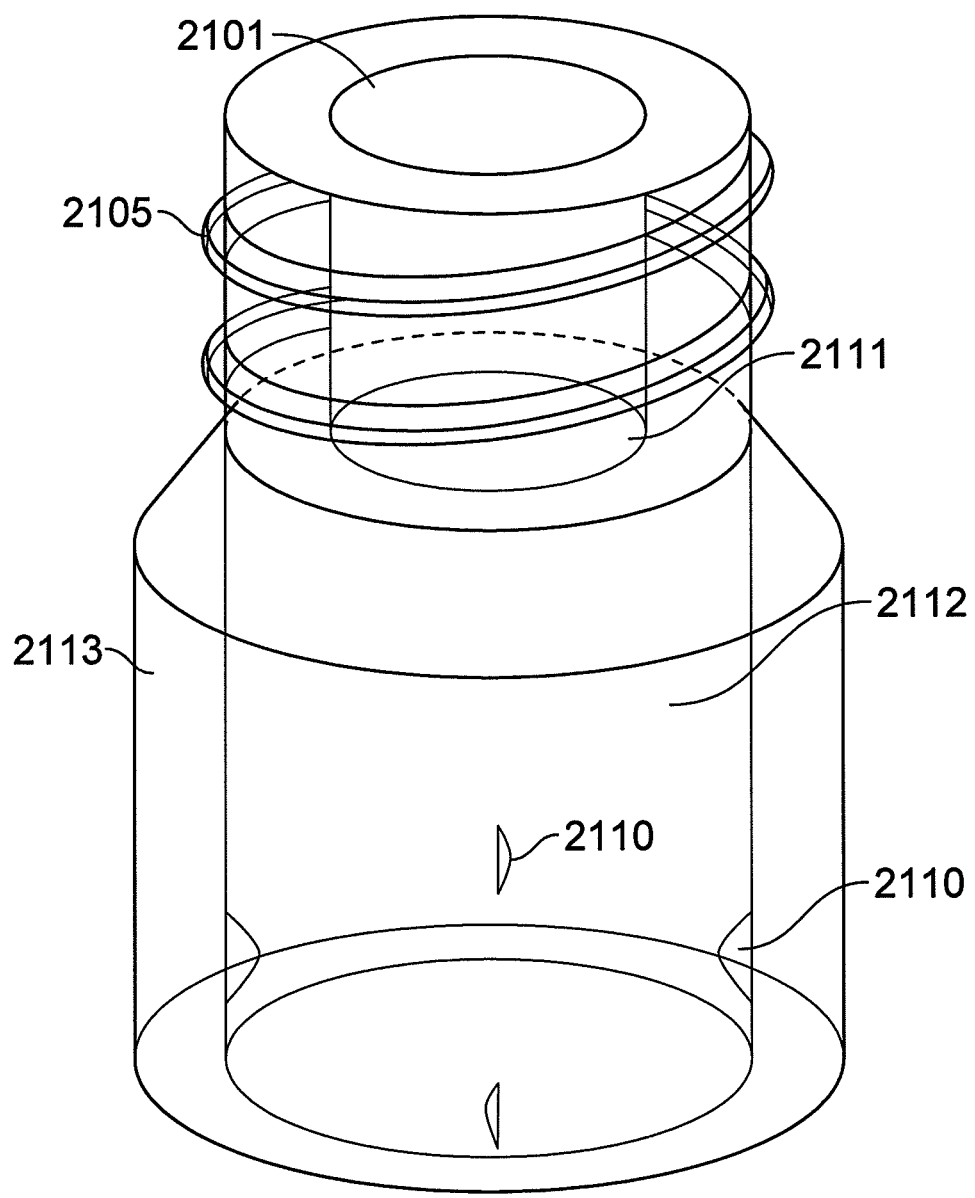
FIG. 16 shows components of a fluid delivery device housing body according to some embodiments.

FIG. 16 shows a housing body (2113) separately and in detail. In the embodiment shown the walls (2113) are made of hard plastic. It has an orifice (2101) which interfaces with the tip of any standard medical syringe or intravenous tubing. The outside wall has screw grooves (2105) to attach a luer lock syringe tip to hold it on the administration device. The orifice (2101) opens into the valve chamber (2112) through an opening (2111). The inner diameter of the valve housing is greater than or equal to the diameter of the syringe tip or intravenous tubing through which the fluid is injected. In other embodiments, one of the orifice 2101 may be configured to only interface with enteral devices such as enteral connectors or enteral tapered syringes.

Figure 17B:
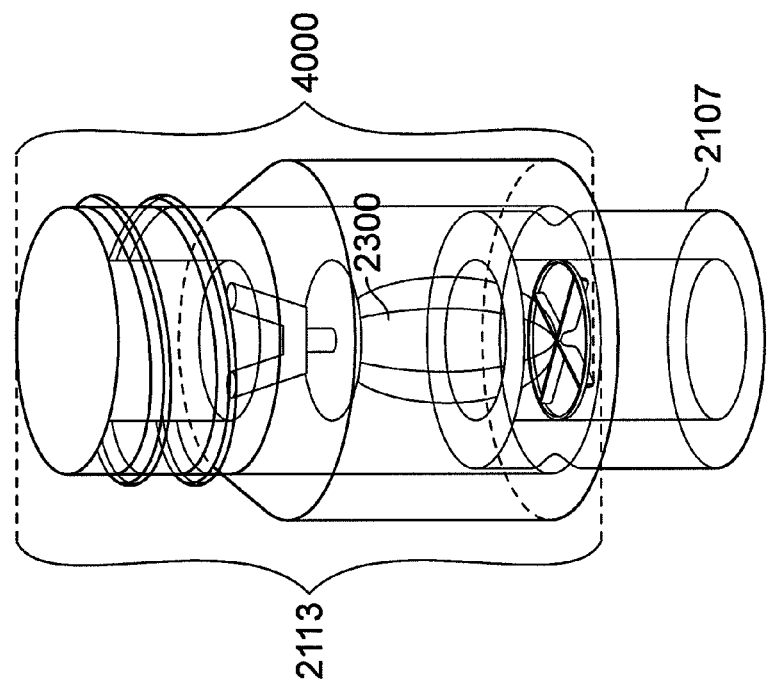
FIGS. 17a-17b show the components of one embodiment of a turbulent flow fluid delivery device. A transfer tube is held to the device by being squeezed between the base of a knob-valve-spring turbulating mechanism and the inner wall of a housing body.
Figure 17A:
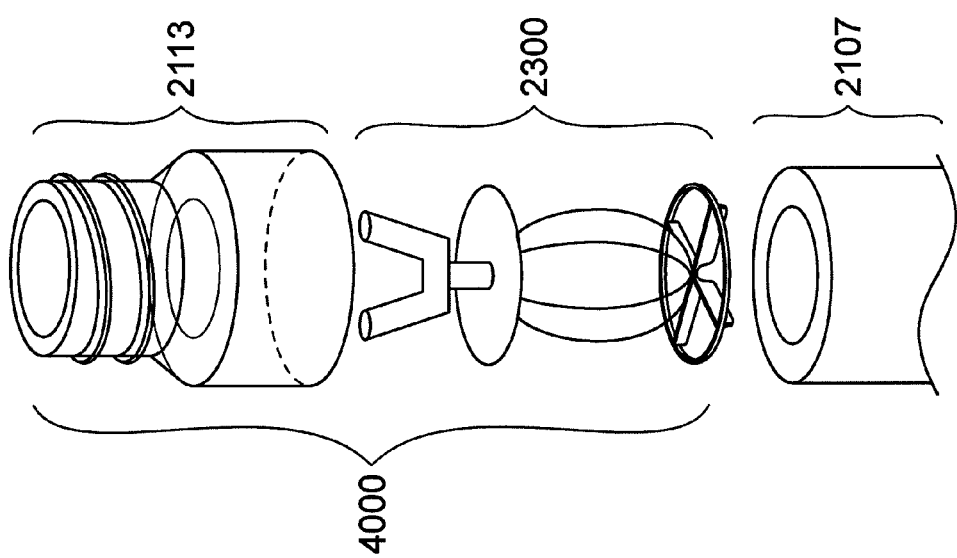

FIGS. 17a-17b show the main components of the non-clogging fluid delivery device 4000. The fluid delivery device 4000 includes a valve assembly 2300. As shown, the valve housing body (2113) is secured to a fluid transport tube (2107) at (2106) by wedges (2110) on the inner wall of the housing body within the valve chamber. These wedges push the tube against the anchoring support turbulator (2108) creating a tight hold and seal. In other embodiments, the device 4000 may be anchored to the tube in other ways, such as a screwing device or attached by an adhesive.

In another aspect, embodiments described provide for methods of enteral fluid or medication administration. In some embodiments, the method includes the steps of providing an enteral administration port and coupling the port to an enteral-type device (e.g. enteral tapered syringe or connector) to form a mated sealed connection between the port and the enteral-type device. In some embodiments, the port includes an inlet section that restrictively couples only to enteral-type devices. Once coupled, a positive pressure is applied from the enteral-type device to depress, compress, deflect, or otherwise move a valve in the port to an open state. In some embodiments, the positive pressure distally pushes the valve to an open state. In other embodiments, the valve is opened by physically engaging or pushing against a valve opening element on the valve. Once open, fluid can be introduced into and transmitted through the port. For example, the methods contemplated can include the step of instilling medication into a patient's body cavity (e.g. rectum) by administering the medication from the enteral tapered syringe through the administration port and into the patient.

In further embodiments, the method includes producing or causing turbulent fluid flow as fluid passes through the port. The turbulent fluid flow may be produced by turbulators in the port, such as those described. Additionally, some embodiments include the steps of maintaining the viscosity of a delivery fluid by causing turbulence in the fluid flow. In other embodiments, the method may include converting a laminar fluid flow to a turbulent fluid flow by flowing the fluid through the port.

In some embodiments, the method includes withdrawing a volume of fluid from the patient using the port. This can be achieved, for example, by applying a negative pressure to remove a volume of fluid from the patient. Once fluid delivery is complete, the port may be removed from the enteral device(s).

It will be apparent to a skilled artisan that the embodiments described herein are exemplary of inventions that may have greater scope than any of the singular descriptions presented. There may be alterations made in these examples without departing from the spirit and scope of the invention disclosed. For example, any portion of a valved enteral administration port may have components with different shapes or designs within different embodiments while still achieving the purpose and utility of the invention. Additionally, the port may be designed differently for valves which connect to intravenous tubes as opposed to enteral tubes.

It can also be appreciated that the dimensions of an enteral syringe or connector may change with industry standards. Thus, the dimensions of port may be changed or modified without detracting from the spirit and scope of this invention. Additionally, any suitable mating features or configurations for an enteral administration assembly or port may be used to restrictively couple the port to an enteral-type device. Although a female inlet is described here as mated to a male counterpart on an enteral device such as an enteral tapered syringe tip, the invention is not limited to this specific configuration. For example, orientations of the mated connection could be reversed where the enteral administration assembly has a male inlet designed to fit only with enteral-type devices with a corresponding female part. Additionally, any type of mechanical attachment or coupling mechanism can be used such that the enteral administration assembly can only form a sealed connection with enteral devices.

In addition, any portion of a turbulent flow valve mechanism may have components with different shapes or designs within different embodiments while still achieving the purpose of turbulent flow within the fluid delivery device and fluid transport tube.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A valved enteral administration assembly comprising:
   a rigid inlet configured to mate with only a first enteral device, the inlet including a seal on an inner diameter thereof configured to form an air and fluid tight seal around the first enteral device and not around a luer device;

a rigid outlet configured to mechanically connect to a lumen of a second enteral device; and a one-way valve mechanism between the inlet and outlet, wherein the one-way valve mechanism is configured to allow fluid to flow from the first enteral device to the second enteral device and to prevent retrograde flow from the lumen of the second device through the inlet when the inlet is mated with the first enteral device.

2. The assembly of claim 1, wherein the rigid inlet comprises an inlet opening and the rigid outlet comprises an outlet opening.

3. The assembly of claim 1, wherein the outlet is configured to permanently interlock to said lumen of the second enteral device.

4. The assembly of claim 1, wherein the rigid inlet comprises holes therein configured to seal when the rigid inlet is mated with the first enteral device.

5. The assembly of claim 1, wherein the inlet comprises a tubular lumen and an inner surface having at least one hole between the valve mechanism and an opening of the inlet.

6. The assembly of claim 1, wherein the outlet comprises an outside surface having a plurality of surface features adapted to maintain the mechanical connection with the lumen of the second enteral device.

7. The assembly of claim 1, wherein the outlet comprises a tapered outer surface having a plurality of protrusions adapted to interlock the lumen of the second enteral device.

8. The assembly of claim 1, wherein an inner surface of the inlet defines a lumen having a tapering cross-section.

9. The assembly of claim 8, wherein the inlet lumen has a first diameter proximal to an inlet opening that is greater than a second diameter proximal to the valve mechanism.

10. The assembly of claim 8, wherein a diameter of the inlet lumen decreases from an opening of the inlet to the valve mechanism along a longitudinal axis of the assembly, the diameter decreasing by an angle of about 1.4 degrees to about 1.7 degrees.

11. The assembly of claim 1, wherein the valve mechanism is configured to produce and maintain turbulent flow of fluids flowing therethrough.

12. The assembly of claim 1, wherein the inlet is configured to mate only with an enteral tapered syringe.

13. The assembly of claim 1, wherein the second enteral device is configured to be inserted into the rectum for rectal medication administration, the second enteral device mechanism including a catheter having a plurality of transmission holes such that medication can be administered through the inlet, valve mechanism, outlet, and transmission holes into the rectum.

14. The assembly of claim 13, wherein the catheter further includes a balloon therearound.

15. The assembly of claim 13, wherein the second enteral device is permanently attached to the rigid outlet.

16. The assembly of claim 1, wherein the one-way valve mechanism is configured to open to allow fluid to flow from the first enteral device to the second enteral device when a fluid pressure is greater on a first side of the valve that is proximate to the inlet than on a second side of the valve that is proximate to the outlet and to close to prevent retrograde flow when a fluid pressure is greater on the second side than the first side.

17. The assembly of claim 1, wherein the one-way valve is further configured to prevent retrograde flow when the inlet is disconnected from the first enteral device.

* * * * *